US011110176B2

(12) United States Patent
Wen

(10) Patent No.: US 11,110,176 B2
(45) Date of Patent: Sep. 7, 2021

(54) COMPOSITION AND METHOD FOR THE PROTECTION OF PROTEINS, CELL COMPONENTS AND CELLS DURING TEMPERATURE STRESS

(71) Applicant: Xin Wen, Alhambra, CA (US)

(72) Inventor: Xin Wen, Alhambra, CA (US)

(73) Assignee: The Board of Trustees of the California State University, Long Beach, CA (US)

( * ) Notice: Subject to any disclaimer, the term of this patent is extended or adjusted under 35 U.S.C. 154(b) by 69 days.

(21) Appl. No.: 15/821,671

(22) Filed: Nov. 22, 2017

(65) Prior Publication Data
US 2018/0147287 A1 May 31, 2018

Related U.S. Application Data

(60) Provisional application No. 62/426,420, filed on Nov. 25, 2016.

(51) Int. Cl.
  *A61K 47/42* (2017.01)
  *C12N 9/96* (2006.01)
  *C12N 1/04* (2006.01)
  *A01N 1/02* (2006.01)
  *A61K 38/28* (2006.01)

(52) U.S. Cl.
  CPC ............ *A61K 47/42* (2013.01); *A01N 1/0221* (2013.01); *A61K 38/28* (2013.01); *C12N 1/04* (2013.01); *C12N 9/96* (2013.01)

(58) Field of Classification Search
  None
  See application file for complete search history.

(56) References Cited

U.S. PATENT DOCUMENTS

| 5,627,051 A * | 5/1997 | Duman ............ C07K 14/43563 435/69.1 |
| 6,392,024 B1 * | 5/2002 | Graham ............ C07K 14/43504 435/252.3 |
| 6,914,043 B1 | 7/2005 | Chapman et al. |
| 8,399,230 B2 | 3/2013 | Van Dyck et al. |
| 9,394,327 B1 | 7/2016 | Wen et al. |
| 2009/0226530 A1 * | 9/2009 | Lassner .................... A61P 9/12 514/1.1 |

FOREIGN PATENT DOCUMENTS

| EP | 1417892 A1 | 5/2004 |
| WO | 03040398 A2 | 5/2003 |
| WO | 2017066454 A2 | 4/2017 |

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Bork (Genome Research, 2000, 10:398-400) (Year: 2000).*
Lazar et al. (Mol. Cell. Biol., 8:1247-1252, 1988) (Year: 1988).*
Guido et al (Curr Med Chem. 2008;15(1):37-46) (Year: 2008).*
Qin et al (Gene 367 (2006) 142-149) (Year: 2006).*
Duman et al (J Comp Physiol B. Apr. 1988; 168(3):225-32) (Year: 1998).*
Chang et al, p. 1, first paragraph (Chang, B.S. and Hershenson, S. 2002. Practical approaches to protein formulation development in "Rationale Design of stable protein formulations—theory and practice" (J.F. Carpenter and M.C. Manning eds.) Kluwer Academic/Plenum publishers, New York. pp. 1-25.) (Year: 2002).*
Jeremias H.R. Kagi et al.; "The Role of Zinc in Alcohol Dehydrogenase"; The Journal of Biological Chemistry; Nov. 1960; pp. 3188-3192; vol. 235, No. 11; http://www.jbc.org.
Ning Li et al.; "Enhancement of Insect Antifreeze Protein Activity by Solutes of Low Molecular Mass"; The Journal of Experimental Biology; 1998; pp. 2243-2251; The Company of Biologists Limited; Great Britain.
Cathy A. Andorfer et al.; "Isolation and Characterization of cDNA Clones Encoding Antifreeze Proteins of the Pyrochroid Beetle Dendroides Canadensis"; Journal of Insect Physiology; 2000; pp. 365-372; Elsevier Science Ltd.
Yih-Cherng Liou et al.; "A Complex Family of Highly Heterogeneous and Internally Repetitive Hyperactive Antifreeze Proteins from the Beetle *Tenebrio molitor*"; Biochemistry; 1999; pp. 11415-11424; American Chemical Society.
Thomas E. Finn et al.; "Serum Albumin Prevents Protein Aggregation and Amyloid Formation and Retains Chaperone-like Activity in the Presence of Physiological Ligands"; The Journal of Biological Chemistry; Jun. 15, 2012; pp. 21530-21540; vol. 287, No. 25; The American Society for Biochemistry and Molecular Biology, Inc.; U.S.A.

(Continued)

*Primary Examiner* — Brian Gangle
*Assistant Examiner* — Andrea K McCollum
(74) *Attorney, Agent, or Firm* — Andrew D. Fortney; Central California IP Group, P.C.

(57) ABSTRACT

Embodiments of the disclosure pertain to compositions containing (i) one or more non-antifreeze proteins or cell components or cells and (ii) one or more antifreeze proteins (AFPs), mimetics thereof, and/or analogs thereof, and a method of stabilizing a biologic (e.g., a protein, microbe, cell component or cell) against temperature stress and aggregation. The AFP may be selected from known antifreeze polypeptides and antifreeze peptides, analogs and mimetics of antifreeze proteins, active fragments of such antifreeze proteins, polypeptide and peptide mimetics, antifreeze peptoids and polymers, and combinations thereof. The non-antifreeze protein, cell component or cell comprises a known protein, cell component or cell used in the pharmaceutical, medical, agricultural, veterinary and/or food industry(ies). The AFP protects the function of the non-antifreeze protein, microbe(s), cell component(s) or cell(s) under temperature stress (e.g., a temperature of −20-60° C.).

18 Claims, 8 Drawing Sheets

Specification includes a Sequence Listing.

(56) References Cited

OTHER PUBLICATIONS

Chuan-Mei Yeh et al.; "Production of a Recombinant Type 1 Antifreeze Protein Analogue by L. lactis and Its Applications on Frozen Meat and Frozen Dough"; Journal of Agricultural and Food Chemistry; 2009; pp. 6216-6223; vol. 57; American Chemical Society.
Sen Wang et al.; "Arginine, a Key Residue for the Enhancing Ability of an Antifreeze Protein of the Beetle *Dendroides canadensis*"; Biochemistry; 2009; pp. 9696-9703; vol. 48; American Chemical Society.
Roger Y. Tam et al.; "Solution Conformation of C-Linked Antifreeze Clycoprotein Analogues and Modulation of Ice Recrystallization"; Journal of American Chemical Society; 2009; pp. 15745-15753; vol. 131; American Chemical Society.
Mathieu Leclere et al.; "C-Linked Antifreeze Glycoprotein (C-AFGP) Analogues as Novel Cryoprotectants"; Bioconjugate Chemistry; 2011; pp. 1804-1810; vol. 22; ACS Publications; American Chemical Society.
Liming Qiu et al.; "A Novel Function—Thermal Protective Properties of an Antifreeze Protein From the Summer Desert Beetle *Microdera punctipennis*"; Cryobiology; 2012; pp. 60-68; Elsevier Inc.
Sen Wang et al.; Expanding the Molecular Recognition Repertoire of Antifreeze Polypeptides: Effects on Nucleoside Crystal Growth; The Royal Society of Chemistry; 2012; pp. 11555-11557, with supporting information at pp. S1-S11; vol. 48; Chem. Commun.
Daniel E. Mitchell et al.; "Antifreeze Protein Mimetic Metallohelices With Potent Ice Recrystallization Inhibition Activity"; Journal of the American Chemical Society; 2017; pp. 9835-9838; ACS Publications; American Chemical Society.
Sen Wang et al.; "Molecular Recognition of Methyl a-D-Mannopyranoside by Antifreeze (Glyco)Proteins"; Journal of the American Chemical Society; 2014; pp. 8973-8981, with supporting information at pp. S1-S5; vol. 136; ACS Publications; American Chemical Society.
Stu Borman; "New Roles for Antifreeze Proteins"; Chemical & Engineering News; 2014; p. 22; vol. 92, Issue 26; American Chemical Society.
Dennis S. Friis et al.; "Low Thermodynamic But High Kinetic Stability of an Antifreeze Protein From Rhagium mordax"; Protein Science; 2014; pp. 760-768; vol. 23, Issue 6; Wiley Online Library.
Kirsty D. Ratanji et al.; "Immunogenicity of Therapeutic Proteins: Influence of Aggregation"; Journal of Immunotoxicology; 2014; pp. 99-109; vol. 11:2; Informa Healthcare USA.
Jose A. Zamalloa; "Role of Conserved Threonine Residues in an Antifreeze Protein From Dendroides canadensis"; Master's Thesis, California State University—Los Angeles, Department of Chemistry and Biochemistry; 2012; 83 pgs.

\* cited by examiner

SEQUENCE LISTING

<160> NUMBER OF SEQ ID NOS: 15

<210> SEQ ID NO 1
<211> LENGTH: 83
<212> TYPE: PRT
<213> ORGANISM: Dendroides canadensis

<400> SEQUENCE: 1

Gln Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
            20                  25                  30

Asn Cys Ile Asn Ala Leu Thr Cys Thr Asp Ser Tyr Asp Cys His Asn
        35                  40                  45

Ala Glu Thr Cys Thr Arg Ser Thr Asn Cys Tyr Lys Ala Lys Thr Cys
    50                  55                  60

Thr Gly Ser Thr Asn Cys Tyr Glu Ala Thr Ala Cys Thr Asp Ser Thr
65                  70                  75                  80

Gly Cys Pro

<210> SEQ ID NO 2
<211> LENGTH: 84
<212> TYPE: PRT
<213> ORGANISM: Dendroides canadensis

<400> SEQUENCE: 2

Gln Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
            20                  25                  30

Asn Cys Asn Asn Ala Leu Thr Cys Thr Asp Ser Tyr Asp Cys His Asn
        35                  40                  45

Ala Glu Thr Cys Thr Arg Ser Thr Asn Cys Tyr Lys Ala Lys Thr Cys
    50                  55                  60

Thr Gly Ser Thr Asn Cys Tyr Glu Ala Thr Thr Ala Cys Thr Asp Ser
65                  70                  75                  80

Thr Gly Cys Pro

<210> SEQ ID NO 3
<211> LENGTH: 71
<212> TYPE: PRT
<213> ORGANISM: Dendroides canadensis

<400> SEQUENCE: 3

Gln Cys Thr Gly Gly Ser Asp Cys Gln Ser Cys Thr Val Ser Cys Thr
1               5                   10                  15

Asp Cys Gln Asn Cys Pro Asn Ala Arg Thr Ala Cys Thr Gly Ser Ser
            20                  25                  30

Asn Cys Ile Asn Ala Leu Thr Cys Thr Asp Ser His Asp Cys His Asn
        35                  40                  45

Ala Glu Thr Cys Thr Arg Ser Thr Asn Cys Tyr Lys Ala Lys Thr Cys
    50                  55                  60

Thr Asp Ser Thr Gly Cys Pro
65                  70

<210> SEQ ID NO 4
<211> LENGTH: 71
<212> TYPE: PRT

<213> ORGANISM: Dendroides canadensis

<400> SEQUENCE: 4

Gln Cys Thr Gly Gly Ser Asp Cys Ser Ser Cys Thr Val Ser Cys Thr
1               5                   10                  15

Asn Cys Gln Asn Cys Pro Asn Ala Arg Val Ala Cys Thr Gly Ser Thr
            20                  25                  30

Asn Cys Ile Asn Ala Leu Thr Cys Thr Asp Ser His Asp Cys His Asn
        35                  40                  45

Ala Glu Thr Cys Thr Arg Ser Thr Asn Cys Tyr Lys Ala Lys Thr Cys
    50                  55                  60

Thr Asp Ser Thr Gly Cys Pro
65                  70

<210> SEQ ID NO 5
<211> LENGTH: 11
<212> TYPE: PRT
<213> ORGANISM: Dendroides canadensis

<400> SEQUENCE: 5

Gln Cys Thr Gly Gly Ser Asp Cys Ser Ser Cys
1               5                   10

<210> SEQ ID NO 6
<211> LENGTH: 11
<212> TYPE: PRT
<213> ORGANISM: Dendroides canadensis
<220> FEATURE:
<221> NAME/KEY: misc_feature
<222> LOCATION: (9)..(9)
<223> OTHER INFORMATION: Xaa can be Arg, Gln or Ser

<400> SEQUENCE: 6

Gln Cys Thr Gly Gly Ser Asp Cys Xaa Ser Cys
1               5                   10

<210> SEQ ID NO 7
<211> LENGTH: 4
<212> TYPE: PRT
<213> ORGANISM: Dendroides canadensis

<400> SEQUENCE: 7

Cys Thr Arg Ser
1

<210> SEQ ID NO 8
<211> LENGTH: 4
<212> TYPE: PRT
<213> ORGANISM: Dendroides canadensis

<400> SEQUENCE: 8

Cys Thr Gly Ser
1

<210> SEQ ID NO 9
<211> LENGTH: 9
<212> TYPE: PRT
<213> ORGANISM: Dendroides canadensis

<400> SEQUENCE: 9

Asp Cys Gln Asn Cys Pro Asn Ala Arg
1               5

```
<210> SEQ ID NO 10
<211> LENGTH: 12
<212> TYPE: PRT
<213> ORGANISM: Dendroides canadensis

<400> SEQUENCE: 10

Asn Cys Gln Asn Cys Pro Asn Ala Arg Val Ala Cys
1               5                   10

<210> SEQ ID NO 11
<211> LENGTH: 9
<212> TYPE: PRT
<213> ORGANISM: Dendroides canadensis
<220> FEATURE:
<221> NAME/KEY: misc_feature
<222> LOCATION: (1)..(1)
<223> OTHER INFORMATION: Xaa can be Arg or Gly
<220> FEATURE:
<221> NAME/KEY: misc_feature
<222> LOCATION: (6)..(6)
<223> OTHER INFORMATION: Xaa can be Ile or Asn

<400> SEQUENCE: 11

Xaa Ser Ser Asn Cys Xaa Asn Ala Leu
1               5

<210> SEQ ID NO 12
<211> LENGTH: 6
<212> TYPE: PRT
<213> ORGANISM: Dendroides canadensis

<400> SEQUENCE: 12

Asn Cys Ile Asn Ala Leu
1               5

<210> SEQ ID NO 13
<211> LENGTH: 9
<212> TYPE: PRT
<213> ORGANISM: Dendroides canadensis
<220> FEATURE:
<221> NAME/KEY: misc_feature
<222> LOCATION: (3)..(3)
<223> OTHER INFORMATION: Xaa can be Tyr or His

<400> SEQUENCE: 13

Asp Ser Xaa Asp Cys His Asn Ala Glu
1               5

<210> SEQ ID NO 14
<211> LENGTH: 6
<212> TYPE: PRT
<213> ORGANISM: Dendroides canadensis

<400> SEQUENCE: 14

Asn Cys Tyr Lys Ala Lys
1               5

<210> SEQ ID NO 15
<211> LENGTH: 5
<212> TYPE: PRT
<213> ORGANISM: Dendroides canadensis

<400> SEQUENCE: 15

Asn Cys Tyr Glu Ala
1               5
```

COMPOSITION AND METHOD FOR THE PROTECTION OF PROTEINS, CELL COMPONENTS AND CELLS DURING TEMPERATURE STRESS

RELATED APPLICATION

This application claims the benefit of U.S. Provisional Pat. Appl. No. 62/426,420, filed Nov. 25, 2016, which is incorporated herein by reference in its entirety.

STATEMENT REGARDING FEDERAL SPONSORSHIP

The present invention was supported at least in part by National Institutes of Health Grant No. SC3GM086249 and National Science Foundation Grant No. 1644917.

SEQUENCE LISTING

The present application incorporates by reference a Sequence Listing in the ASCII text file identified by the file name "CSULA-003_Seqlisting_20210114_ST25.txt", created on Jan. 14, 2021, and having a size of 5,425 bytes.

FIELD OF THE INVENTION

The present invention generally relates to the field of protein stabilization. More specifically, embodiments of the present invention pertain to compositions containing (i) one or more non-antifreeze proteins, cell components, cells, or microbes, and (ii) one or more antifreeze proteins (AFPs), and methods of stabilizing proteins, microbes, cell components and/or cells against heat and freezing using an AFP.

DISCUSSION OF THE BACKGROUND

Antifreeze proteins (AFPs) are found in many organisms that need to survive in subfreezing environments, such as bacteria, fungi, fish, plants, and insects. AFPs lower the freezing point of aqueous solutions or suspensions such as blood without altering their melting point. Of all the organisms that transcribe AFPs, insects appear to exhibit the greatest antifreeze protein activity. Insect AFPs have a relatively high thermal hysteresis value (i.e., the difference between freezing and melting points).

Antifreeze proteins (AFPs) are a group of polypeptides naturally occurring in many cold-adapted organisms (e.g., freezing-avoidance and freezing-tolerant organisms) to allow them to survive at subzero temperatures. Some AFPs are glycoproteins, which are also called antifreeze glycoproteins (AFGPs). AF(G)Ps were first identified in polar fish, and have been found in diverse organisms including microorganisms, plants, insects, and arthropods.

Although there are a variety of AF(G)P structures, they are characterized by their ability to bind to ice and inhibit or slow ice growth and/or ice recrystallization. Therefore, AF(G)Ps are also known as ice-binding proteins (IBP) or ice structuring proteins (ISP).

AFPs can depress the freezing point of water in a non-colligative manner, apparently without changing the melting point of water. The difference between the depressed freezing point and the (unchanged) melting point is termed thermal hysteresis (TH), and the value of TH is usually a measure of the antifreeze activity of AFPs. AFPs from insects are generally more active than AFPs from other species.

AF(G)Ps exhibit remarkable structural and sequential variation among species, which seem to be unrelated to evolutionary relationships among the species. AF(G)Ps often occur as a series of isoforms in a species without close similarities to any other known proteins. A few examples are given below. Type I AFPs are small amphipathic α-helical proteins containing periodically repeating amino acids and their molecular weights are about 3-5 kDa. AF(G)Ps mainly consist of repeat units of two or three amino acids, one of them glycosylated, and AF(G)Ps usually have 4 to 32 repeat units and have a molecular weight from 2 kDa to 34 kDa. Type II and Type III AFPs are globular proteins without repeating units and they consist of varied secondary structures. Their molecular weights are about 14-16 kDa and about 6 kDa, respectively.

Mimetics of AF(G)Ps have been synthesized, and various engineered AF(G)Ps (e.g., mutations), fragments of AF(G)Ps, active mimetic fragments of AF(G)Ps have been reported. Natural or engineered AF(G)Ps (e.g., mutations), active fragments of AF(G)Ps, mimetics of AF(G)Ps, their active mimetic fragments, and combinations thereof can also bind to ice crystals to inhibit or reduce growth and/or recrystallization of ice.

AF(G)Ps are usually very stable and remain active under extreme conditions (e.g., extreme temperatures and pH variations). For example, an AFP in an overwintering perennial ryegrass, *Lolium perenne*, (a plant AFP having less TH value than fish/insect AF(G)Ps, while better at preventing ice recrystallization) is stable at 100° C. (Sidebottom et al., *Nature* [2000] 405, 256). Insect AFPs (both natural and recombinant) have much higher TH values than plant AFPs, and they can also resist extreme temperatures and extreme pHs. For example, AFPs from *Dendroides canadensis* are still active in a very wide temperature and pH ranges (e.g., temperature from −90° C. to +90° C., pH from pH 1 to pH 12; see Li N, Andorfer C A, Duman J G (1998), "Enhancement of insect antifreeze protein activity by solutes of low molecular mass," *J Exp Biol* 201:2243-2251). Generally, AF(G)Ps can remain active at high temperatures (e.g., 30° C. above room temperature; see Friis et al., "Low thermodynamic but high kinetic stability of an antifreeze protein from *Rhagium mordax*," *Protein Science* 2014 vol. 23:760-768).

The applications of AFPs can reach diverse fields, such as food, pharmaceutical, medicine, agriculture industries (Chapman et al., "Frozen food products comprising antifreeze protein (AFP) type III HPLC 12," U.S. Pat. No. 6,914,043; Daniel et al., "Ice cream confection containing an antifreeze protein," European Pat. Publ. No. 14 17 892 A1).

AF(G)Ps in controlling the crystallization of non-ice-like compounds (ice-like compounds include ice and gas hydrates) have been reported recently (see, e.g., Xin Wen and Sen Wang, Nucleoside crystals, crystal nucleation and growth control with antifreeze proteins, U.S. Pat. No. 9,394,327 B1; *Chemical & Engineering News* (2014), Vol. 92, Iss. 26, p. 22; Wang et al., "Expanding the molecular recognition repertoire of antifreeze polypeptides: effects on nucleoside crystal growth," *Chem. Commun.* 48:11555-11557 [2012]). The correlation between the antifreeze activity of AFPs and their effects on controlling the crystallization of non-ice-like compounds have also been demonstrated (see, e.g., Wang, S. et al., "Molecular Recognition of Methyl α-D-Mannopyranoside by Antifreeze (Glyco)Proteins," *J. Am. Chem. Soc.* [2014], 136: 8973-8981). These new roles for AF(G)Ps greatly expand the applications of AF(G)Ps.

Proteins (e.g., enzymes, hormones, antibodies, etc.) are commonly used as laboratory reagents and nutritional supplements and in therapeutic applications. During storage and transport, proteins may become unstable due to thermal or temperature stressors (e.g., heat or freezing). This can increase the cost of the protein (e.g., more protein must be used to achieve the same effectiveness, or the shelf-life may shorten) and/or reduce the effectiveness of protein-based products. As the temperature and/or amount of heat increases, enzymes may become denatured, thereby affecting the rates of the reactions they catalyze.

There are many commonly known protein stabilizers and protectants available in the market. Some of these stabilizers include sugars, salts, amino acids, other proteins, and polymers. In the presence of such excipients, proteins may still demonstrate instability.

U.S. Pat. No. 9,394,327 discloses the use of AFPs to inhibit or prevent the crystallization of nucleoside compounds. AFPs can efficiently inhibit nucleation and can modify single crystal growth of compounds having non-ice-like crystalline structures such as nucleosides and sugars.

Many organisms produce a complex family of heterogeneous AFPs. The yellow mealworm, *Tenebrio molitor*, produces antifreeze proteins known as TmAFPs (e.g., one or more of 17 known isoforms of TmAFPs; see Liou Y. et al., "A Complex Family of Highly Heterogeneous and Internally Repetitive Hyperactive Antifreeze Proteins from the Beetle *Tenebrio molitor*," *Biochemistry* 1999, 38, 11415-11424). There are at least 13 known AFPs from *Dendroides canadensis* (DAFPs) containing varying numbers and sizes of repeat units with sizes of 7-17 kDa (Andorfer C A and Duman J G, "Isolation and characterization of cDNA clones encoding antifreeze proteins of the pyrochroid beetle *Dendroides canadensis*," *Journal of Insect Physiology* 46 (2000), 365-372).

Seasonal variations in AFP transcript levels have been observed. One study (Andorfer et al., "Isolation and characterization of cDNA clones encoding antifreeze proteins of the pyrochroid beetle *Dendroides canadensis*," *J. Insect Physiol.*, vol. 46 [2000], pp. 365-372) discloses peak levels of the dafp-1 transcript in *D. canadensis* (an overwintering pyrochroid beetle) in early winter, and negligible levels of DAFP-1 RNA transcript in the beetle in summer. Andorfer discloses that a different DAFP (DAFP-7) is predominantly present in the beetle in summer, and there are high levels of dafp-7 transcript in the summer beetle. Andorfer discloses seasonally differential expression of different AFP isoforms in the beetle, and the correlation between low levels of thermal hysteresis in the summer beetle to the presence of DAFP-7 in the summer beetle at high levels. Another study (Qiu et al., "A novel function—Thermal protective properties of an antifreeze protein from the summer desert beetle *Microdera punctipennis*," *Cryobiology*, vol. 66 [2013], pp. 60-68) discloses transcripts of MpAFPS77 isolated from the desert beetle *Microdera punctipennis* in summer, increased amounts of MpAFP mRNA transcripts found in desert beetles after heat shock, little protective effect of MpAFPS77 at low temperatures (e.g., 4° C.), and the thermal hysteresis value of MpAFPS77 much less than that of MpAFP149 (an isoform from winter specimens of *M. punctipennis*), suggesting that MpAFPS77 may play a role in heat protection for the summer beetle.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention pertain to compositions containing (i) one or more non-antifreeze proteins, cell components, microbes or cells including such non-antifreeze proteins, and (ii) one or more antifreeze proteins (AFPs) in an amount effective to stabilize the non-antifreeze protein(s), or cells, cell components or microbes. The composition may further comprise a liquid and/or solid excipient or carrier. Optionally, the AFP may be in combination with at least one pharmaceutically, nutritionally, or generally acceptable excipient, carrier, adjuvant and/or additive.

In one aspect, the AFP is selected from the group consisting of fish AFPs (e.g., type I AFPs, type II AFPs, type III AFPs, type IV AFPs), plant AFPs, insect AFPs, arthropod AFPs, bacteria AFPs, fungi AFPs, fish, plant and insect antifreeze glycoproteins (AFGPs), antifreeze polypeptides and peptides, active fragments of AFPs, AFGPs, antifreeze polypeptides and antifreeze peptides, mimetics of AFPs, AFGPs, antifreeze polypeptides and antifreeze peptides, active fragments of antifreeze protein, glycoprotein, polypeptide and peptide mimetics, and combinations, analogs and homologs thereof. The selected AFP is predominantly present in the organism in winter.

In other examples, the AFP may have an amino acid sequence of the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, $R^1$ is H, $C_{1-6}$ alkyl, $R^3$—C(=O)— or $R^3$—OC(=O)—, x is an integer of at least 3, $R^2$ is OH, $C_{1-6}$ alkoxy, $R^4$—NH— or $R^4_2$N—, $R^3$ is $C_{1-6}$ alkyl, $C_{6-10}$ aryl, or $C_{1-6}$ alkyl or $C_{6-10}$ aryl substituted with one or more halogen atoms and/or $C_{1-4}$ alkyl groups, and $R^4$ is $C_{1-4}$ alkyl. The AFP or AFGP (AF[G]P) may be natural, engineered, or synthesized.

The antifreeze protein, glycoprotein, polypeptide and peptide analogs may have (1) an amino acid sequence that differs from the amino acid sequence of the native protein, glycoprotein, polypeptide or peptide by a limited number of amino acids (e.g., the number may be 30% or less than the total number of amino acids in the sequence, such as from 5 to 30 amino acids) and (2) at least the same or similar (e.g., >50% of the) antifreeze activity as the native protein, glycoprotein, polypeptide or peptide. The antifreeze protein, glycoprotein, polypeptide and peptide analogs may also include those with the same amino acid sequence of the native protein, glycoprotein, polypeptide or peptide, but modified with non-amino acid substitutions and/or end groups (e.g., amide or ester groups on a carboxylic acid, carboxyl groups on an amine, thiol or alcohol, one or more alkyl groups on an amide, etc.). Antifreeze protein, glycoprotein, polypeptide and peptide analogs may also include those disclosed in U.S. Pat. No. 9,394,327, the relevant portions of which are incorporated herein by reference, and antifreeze peptoids and polymers such as those disclosed in International Pat. Publ. No. WO 2017/066454, Tam R. Y. et al., "Solution Conformation of C-Linked Antifreeze Glycoprotein Analogues and Modulation of Ice Recrystallization," *J. Am. Chem. Soc.* (2009), 131:43, 15745-15753, 139:29, 9835-9838, Leclere, M. et al., "C-Linked Antifreeze Glycoprotein (C-AFGP) Analogues as Novel Cryoprotectants" *Bioconjugate Chem.*, 2011, 22 (9), pp 1804-1810, Yeh, C-M, et al., "Production of a Recombinant Type 1 Antifreeze Protein Analogue by *L. lactis* and Its Applications on Frozen Meat and Frozen Dough," *J. Agric. Food Chem.* 2009, 57, 6216-6223, and in Mitchell, D. E., et al., "Antifreeze Protein Mimetic Metallohelices with Potent Ice Recrystallization Inhibition Activity," *J. Am. Chem. Soc.* (2017) 139:29, 9835-9838, the relevant portions of which are incorporated herein by reference.

The AFP may comprise an insect AFP such as a DAFP or TmAFP. DAFPs include DAFP-1 (SEQ ID NO 1), DAFP-2 (SEQ ID NO 2), DAFP-4 (SEQ ID NO 3) and DAFP-6 (SEQ ID NO 4). The insect AFP may also include a DAFP isoform having at least 3 Thr-X-Thr units (e.g., 4-6 such units), where X is a sequence of from 1 to 3 amino acids and which may include Cys. The DAFP isoforms include proteins having an amino acid sequence of the formula A-(Thr-X-Thr-Y)$_z$-B, where A is a sequence of at least 1 amino acid (e.g., 8-12 amino acids, such as Gln-Cys-Thr-Gly-Gly-Ser-Asp-Cys-Ser-Ser-Cys [SEQ ID NO 5]), Y is a sequence of 1-12 amino acids (see, e.g., SEQ ID NOS 1-4), z is an integer of from 3 to 32 (e.g., 3 to 8), and B is a sequence of 1-5 amino acids (e.g., Gly-Cys-Pro).

Alternatively, the AFP may be selected from the group consisting of fish AFPs (e.g., type I AFPs, type II AFPs, type III AFPs and type IV AFPs), plant AFPs and AFPs and antifreeze glycoproteins (AFGPs) having an amino acid sequence of the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, $R^1$ is H, $C_{1-6}$ alkyl, $R^3$—C(=O)— or $R^3$—OC(=O)—, x is an integer of at least 3, $R^2$ is OH, $C_{1-6}$ alkoxy, $R^4$—NH— or $R^4{}_2$N—, $R^3$ is $C_{1-6}$ alkyl, $C_{6-10}$ aryl, or $C_{1-6}$ alkyl or $C_{6-10}$ aryl substituted with one or more halogen atoms and/or $C_{1-4}$ alkyl groups, and $R^4$ is $C_{1-4}$ alkyl.

When the AFP is one or more of the AFPs or AFGPs having the amino acid sequence of the formula $R^1$-(AA1-AA1-AA2)$_x$-$R^2$, each AA1 may independently be Ala, Gly, Val, Leu, or Ile, and in some embodiments, the amino acid sequence may have the formula $R^1$—[Ala-Ala-Thr]$_x$-$R^2$, where 0-10% of the alanines in the formula $R^1$-[Ala-Ala-Thr]$_x$-$R^2$ are replaced with glycine or leucine and 0-10% of the threonines in the formula $R^1$-[Ala-Ala-Thr]$_x$-$R^2$ are replaced with serine or tyrosine. Furthermore, x may be 8-100, 10-60, or 30-50 and/or 10-12. The AFPs or AFGPs having the amino acid sequence of the formula $R^1$-(AA1-AA1-AA2)$_x$-$R^2$ may include one or more mono- or disaccharides (any of which may further include an acetylamido or other $C_{1-4}$ alkanoylamido groups in place of an OH group) linked to a threonine (or serine) hydroxyl group through a glycosidic linkage.

The non-antifreeze protein may comprise any known protein other than an AFP, including proteins used in the pharmaceutical, veterinary and food industries. For example, the non-antifreeze proteins to be stabilized may include enzymes, hormones (e.g., insulin, growth hormones, etc.), antibodies (e.g., IgG, IgE, IgA, IgM and/or IgD antibodies), growth factors, viral and bacterial proteins (e.g., used in vaccinations or having autoimmune stimulating properties), nutrient proteins, and food proteins. Examples of non-antifreeze proteins in nutritional and food applications may include proteins found in solid compositions such as whey protein and/or powder, tofu and meat-based products such as sausage, and proteins found in liquid compositions such as milk, fermented yogurt beverages and protein shakes. The cell components may comprise any known cell components other than an AFP (e.g., a cell component that may include or produce a nonantifreeze protein), including coenzymes (e.g. CoQ, NADH), nucleosides, polynucleic acids, and lipids used in the pharmaceutical, veterinary and food industries. The cells may comprise any known cells including bacteria cells, plant cells, blood cells (e.g., serum), stem cells, egg cells, fungal cells, mold cells, animal cells, human cells, etc., used in pharmaceutical, veterinary and food industries, including live or dead bacteria and viruses used in vaccinations. The microbes may comprise microorganisms that are beneficial to health (e.g., probiotics).

A further aspect of the present invention relates to a formulation comprising the present composition in a pharmaceutically or nutritionally acceptable solid or liquid excipient. The pharmaceutically acceptable liquid excipient may comprise deionized and/or distilled water (e.g., a biologically-compatible and/or isotonic saline solution). The pharmaceutically acceptable solid excipient may comprise a diluent or bulking agent such as lactose or starch, a binder such as a saccharide, sugar alcohol, gelatin or polyvinylpyrrolidone (PVP), a coating such as cellulose, or a disintegrant such as cross-linked polyvinylpyrrolidone or cross-linked carboxymethyl cellulose. The ratio of AFP to the sample volume may be in the range of 1:20 to 1:5,000,000 (weight to volume, or w/v) (or any value or range of values therein, such as 1:50, 1:100 or 1:1000 to 1:200,000). Alternatively, the ratio of AFP to non-antifreeze protein may be in the range of 10:1 to 1:1000 by weight (or any value or range of values therein).

In some embodiments, the excipient is the liquid excipient, and the excipient may comprise deionized and/or distilled water. In further (or alternative) embodiments, the formulation may comprise a pharmaceutically or nutritionally acceptable salt and/or saccharide. In other embodiments, the excipient is the solid excipient, and the excipient may comprise a diluent, disintegrant, binder, lubricant, or glidant. For example, the solid excipient may be selected from the group consisting of sucrose, lactose, cellulose, hydroxypropyl methylcellulose, starches, gelatin, xylitol, sorbitol, maltitol, shellac, zein, sodium starch glycolate, croscarmellose sodium, polyvinylpyrrolidone, polyethylene glycol, xanthan gum, magnesium stearate, and colloidal $SiO_2$. Optionally, the AFP may be in combination with at least one pharmaceutical, nutritional, or acceptable excipient, carrier, adjuvant and/or additive.

By adding an AFP, the protein, cell component(s) or cell(s) can be protected from thermal or temperature (e.g., hot and/or cold) stresses, and thus, heat and cold stress-related changes in the structure and/or function of the protein, cell component(s) or cell(s) (e.g., the rate of a reaction catalyzed by an enzyme, or the taste and texture of a protein-based foodstuff or beverage) may be prevented. By adding an AFP or AFGP, the storage stability of a protein formulation (e.g., a pharmaceutical formulation including a drug, or a foodstuff) can be prolonged, especially during hot summer months or freezing winter months.

An even further aspect of the present invention relates to a method of protecting a protein from thermal or temperature stress, comprising combining an AFP with a non-antifreeze protein (e.g., in a mass ratio of the AFP to the non-antifreeze protein, cell component or cells to form a mixture, and storing the mixture for a minimum length of time. The mixture may be stored at least temporarily at a temperature at which the protein is stressed in the absence of the AFP. The minimum length of time may be 1 hour, 1 day, 1 week, 1 month, or longer. The mixture may be solid (e.g., further including a solid excipient or carrier) or liquid (e.g., further comprising a carrier and/or excipient that is liquid at ambient temperatures, such as 15-25° C.). The liquid excipient may (further) comprise deionized and/or distilled water (e.g., a biologically-compatible and/or isotonic saline solution). The ratio of AFP to the sample volume may be in the range of 1:20 to 1:5,000,000 (w/v) (or any value or range of values therein). Alternatively, the ratio of AFP to non-antifreeze protein may be in the range of 10:1 to 1:1000 by weight (or any value or range of values therein).

For example, the minimum length of time may be double (or quadruple, or 10 times, or any other value greater than double) a length of time during which the non-antifreeze protein and/or the cell component maintains a minimum commercial activity, or the cell and/or the microbe maintains a minimum commercial viability, in the absence of the AFP. In various cases, the minimum length of time may be 1 day, 1 week, 1 month, or any other length of time greater than 1 day.

In general, the method comprises storing the mixture at a temperature of from 4° C. to 25° C. However, in many cases, the comprises storing the mixture at least temporarily at a temperature at which a structure and/or function of the non-antifreeze protein, the cell component, the cell, the microbe, or the combinations may be affected in the absence of the AFP. For example, the mixture may be stored at least temporarily at a temperature of 25° C. or more (e.g., 30° C. or more, or any other temperature >25° C. or more), or at or below 4° C. (e.g., <0° C., or any other temperature below 0° C. or less).

Some embodiments of the method comprise combining the antifreeze protein and the non-antifreeze protein. In such embodiments, the non-antifreeze protein may comprise an enzyme, hormone, growth factor, antibody, vaccination protein, therapeutic protein, or nutrient protein. Alternatively, the method may comprise combining the AFP with a foodstuff or beverage, in which case the non-antifreeze protein may be a component of the foodstuff or beverage.

The prior studies neither disclose nor suggest the fact that AFPs (which have gene transcripts that are negligible during the summer, or genes that are transcribed only in cold seasons) protect enzymes or other proteins from heat stress, nor do they disclose or suggest any effective ratio of AFP to protein or enzyme in a solution or composition in order to protect the protein or enzyme from heat or cold.

These and other advantages of the present invention will become readily apparent from the detailed description of various embodiments below.

DETAILED DESCRIPTION

Figure 1:
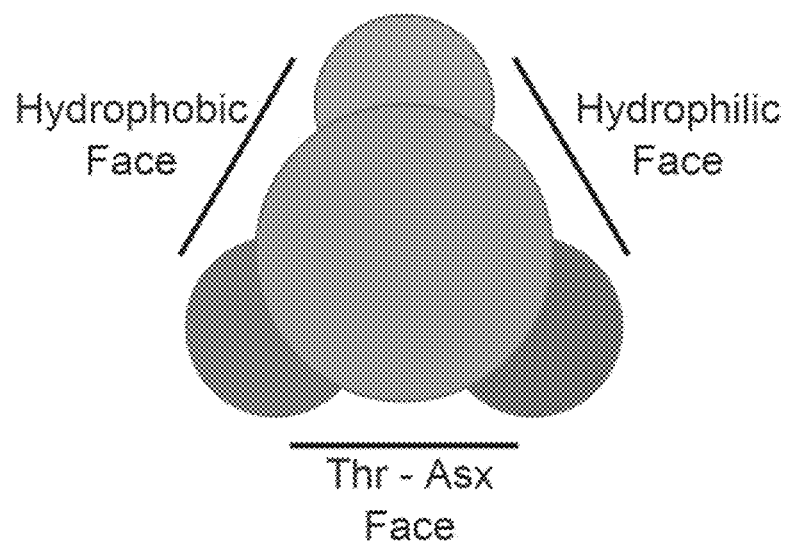
FIG. 1 shows the faces of the 3D structure of type I AFPs.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

The present invention relates in part to the use of antifreeze proteins for the protection of non-antifreeze proteins, or cell components or cells including the non-antifreeze proteins, during heat stress. The present invention includes a method of protecting the non-antifreeze proteins, cell components or cells from heat stress by combining an AFP with the non-antifreeze protein, cell component(s) or cell(s) (e.g., in solution or as a mixture). The AFP may be combined at a mass ratio of AFP to non-antifreeze protein of from 10:1 to 1:1000 (or any value or range of values therein). Alternatively, the AFP may be present at a ratio of the AFP mass to the volume of the composition in a range of 1:20 to 1:5,000,000. The present invention has great economic potential. Among other things, it advances methods of stabilizing proteins used in laboratory, medical, veterinary, food and therapeutic applications. The invention, in its various aspects, will be explained in greater detail below with regard to exemplary embodiments.

A common sugar that protects proteins under thermal stress or temperature stress is known as trehalose. It has been shown that small amounts of this sugar (e.g., at a mass ratio of at least 10:1) protect enzymes under heat stress. Like trehalose, antifreeze proteins exhibit protective behaviors towards proteins and enzymes, allowing them to maintain their structure and/or catalytic activity by preventing their denaturation during periods of temperature stress. AFPs are potentially more effective at protection of proteins under thermal or temperature stress than trehalose. For example, AFPs can maintain the integrity of the enzyme lactate dehydrogenase at temperatures of 46-50° C. at a variety of AFP concentrations. Additionally, a relatively small amount of AFP protects the enzyme. For example, at least some protection is provided and/or expected at a AFP:non-AFP mass ratio of from 10:1 to 1:100 (or at a weight:volume ratio of the AFP to the sample/composition in a range of 1:20 to 1:5,000,000). For example, DAFP-1 has been shown experimentally to protect lactate dehydrogenase optimally at a mass ratio in the range of 1:3 to 1:1. Lactate dehydrogenase is a known biomarker and is ubiquitous in nearly all living cells, suggesting that the present invention can be rather versatile.

The term "AFP" may defined herein as the cumulative group consisting of natural antifreeze proteins or antifreeze polypeptides or antifreeze peptides that are predominantly present or expressed in the organism (e.g., at a peak level) in winter; engineered antifreeze proteins, antifreeze polypeptides and antifreeze peptides based on the natural forms; active fragments of antifreeze proteins, antifreeze polypeptides and antifreeze peptides based on the natural forms; mimetics of antifreeze proteins, antifreeze polypeptides and antifreeze peptides based on the natural forms; their active mimetic fragments; analogs and homologs of antifreeze proteins, antifreeze polypeptides and antifreeze peptides based on the natural forms; and combinations thereof. For example, the AFP may be (i) present at a peak level in winter, (ii) encoded by a gene that is expressed in the corresponding natural organism at a peak level in winter (and, optionally, that is expressed at a relatively low level in summer), or (iii) an analog, active fragment or mimetic of such an AFP. The foregoing term "antifreeze" may be defined as having or providing one or more antifreeze properties or characteristics (e.g., thermal hysteresis, ice binding, ice structuring, inhibition of ice growth, inhibition of ice recrystallization), which may be a threshold level or value of the property or characteristic. The term "ice-like crystalline structures" may be defined as ice, gas hydrates and clathrate hydrates that are in the solid phase. The term "critical ratio" may be defined as the molar ratio of the substance or additive being protected from thermal or temperature stress to the AF(G)P compound that completely inhibits the growth of crystals or that suppresses heat-induced loss of activity.

One application of the present invention includes the preservation of food. Considering the concentration of AFPs that exhibit protective behaviors (e.g., a mass ratio of about 1 part AFP to about 1-10 parts non-antifreeze protein), they can potentially replace other reagents used to preserve foods, and potentially at a lower cost and/or with fewer health-related side effects. During the transport of foods, the food can be exposed to a wide range of temperatures, and the versatility of AFPs to protect non-antifreeze proteins from thermal or temperature stress can potentially alleviate problems associated with such temperature variations. The stabilization offered by AFPs can help minimize costs of additional transportation equipment, such as insulating and/or refrigerating mechanisms in an airplane, truck, train or ship.

The present invention may be used in medical applications, for example, that may be geared towards preserving cells or improving the function of cells over a period of time. For example, if a power failure occurs during a hot summer month (e.g., the temperature approaches 50° C.) and affects a medical or scientific laboratory, proteins stored in refrigerators that would otherwise be damaged may retain their potency in the presence of an AFP. Additionally, this technology can be used to protect protein-based drugs and vaccines during their transport, potentially increasing the shelf life and quality of drugs during their storage and transport process.

In various embodiments, the present method and composition utilizes AFPs such as DAFPs (including DAFP-1 (SEQ ID NO 1), DAFP-2 (SEQ ID NO 2), DAFP-4 (SEQ ID NO 3) and DAFP-6 (SEQ ID NO 4)), as well as other antifreeze proteins including fish AFPs and other insect AFPs (e.g., TmAFPs). DAFPs and TmAFPs are hyperactive AFPs (e.g., having a relatively high thermal hysteresis value) and are very stable proteins. They both have a β-helical (i.e., β-solenoid) structure and share high sequence identities (>40%) and high sequence similarities (>60%).

In further embodiments, fish AFPs comprising or consisting of repeated Ala-Ala-Thr units (e.g., having the formula $R^1$-[Ala-Ala-Thr]$_x$-$R^2$, where $R^1$ is H, $C_{1-6}$ alkyl, $R^3$—C(=O)— or $R^3$—OC(=O)—, x is an integer of at least 3 [e.g., 8-100, 10-50, or any value or range of values therein], $R^2$ is OH, $C_{1-6}$ alkoxy, $R^4$—NH— or $R^4_2$N—, $R^3$ is $C_{1-6}$ alkyl, $C_{6-10}$ aryl, or $C_{1-6}$ alkyl or $C_{6-10}$ aryl substituted with one or more halogen atoms (e.g., F or Cl) and/or $C_{1-4}$ alkyl groups, and $R^4$ is $C_{1-4}$ alkyl) may also be effective in the present invention. Furthermore, other amino acids with similar physical and/or chemical properties may be substituted for one or more of the alanines or threonines in one or more of the units. Accordingly, fish AFP isoforms suitable for use in the present method and composition include those having the formula $R^1$-(AA1-AA1-AA2)$_x$-$R^2$. Each AA1 is independently Ala, Asn, Gly, Val, Leu Pro, Phe, Thr, Tyr, or Ile, each AA2 is independently Thr or Ser or Tyr, and $R^1$ and $R^2$ are as described above. In some examples, no more than 10% of the alanines or threonines in the formula R'-[Ala-Ala-Thr]$_x$-$R^2$ are replaced with a different amino acid (e.g., Ala replaced with Gly and/or Thr replaced with Ser). The present fish AFPs and isoforms thereof may be glycosylated (e.g., with one or more β-d-galactosyl(1→3)-α-N-acetylgalactosamine or other mono- or disaccharide [any of which may include an acetylamido or other $C_{1-4}$ alkanoylamido groups in place of an OH group] linked to the AA2 hydroxyl group through a glycosidic linkage.

The AFP may also be selected from other fish AFPs and AFGPs (e.g., type I-IV AFPs and AFGPs), plant AFPs, bacterial AFPs, and fungus AFPs that are present or expressed predominantly in winter. Type I AFPs include an alanine-rich α-helix. Type II AFPs and type III AFPs are unrelated globular proteins having no repetitive characters (e.g., amino acid sequences). Type II AFPs have a lectin-like fold with mixed α, β, and loop structures, while type III AFPs shows a compact fold with short and/or irregular β-strands. AFGPs are glycoproteins, and may adopt a polyproline II structure.

Both O-linked and C-linked analogs of antifreeze glycoprotein have been prepared. Antifreeze protein, glycoprotein, polypeptide and peptide analogs may also include those disclosed in U.S. Pat. No. 9,394,327, the relevant portions of which are incorporated herein by reference, and antifreeze peptoids and polymers such as those disclosed in International Pat. Publ. No. WO 2017/066454 and in Mitchell, D.

E., et al., "Antifreeze Protein Mimetic Metallohelices with Potent Ice Recrystallization Inhibition Activity," *J. Am. Chem. Soc.* (2017) 139:29, 9835-9838, the relevant portions of which are incorporated herein by reference. The AFP, AFP analog, or AFP mimetic inhibits or controls crystallization of the carbohydrate (e.g., during the storage of the solution of the carbohydrate or the analog thereof, during the freeze-drying of a formulation using the carbohydrate or the analog thereof) and stabilizes a solution or formulation including the carbohydrate or the carbohydrate analog.

Despite their different structures, the AFPs and AFGPs are thought to have a relatively flat region or surface in their structures (see, e.g., FIG. 1). These relatively flat surfaces of AFPs may help the AFPs to fulfill one of their original evolutionary functions (e.g., recognizing specific surfaces of ice crystals in order to halt their propagation).

Type I AFPs can be found in fish such as winter flounder, longhorn sculpin and shorthorn sculpin. Its three-dimensional structure has been determined. Type I AFPs generally consist of a single, long, amphipathic alpha helix, about 3.3-4.5 kDa in size. There are three faces to the 3D structure: the hydrophobic, hydrophilic, and Thr-Asx faces (see, e.g., FIG. 1). Type III AFPs exhibit similar overall hydrophobicity at ice binding surfaces to type I AFPs. They are approximately 6 kD in size. One type III AFP is fish AFP III, a prototypical globular AFP having size (or molecular mass) of 7 kDa that is present in members of the fish subclass Zoarcoidei.

In the AFP analogs and homologs, the mutations or differences may not be in amino acids known to be essential for activity of the (poly)peptide. Preferably any differences in the amino acid sequence of an AFP analog or homolog are silent mutations, whereby the substitutions are conservative substitutions that do not alter the hydropathy profile of the polypeptide and thus presumably do not severely influence the polypeptide structure and the activity. For example, an amino acid with a hydrophobic side chain is preferably exchanged only with another amino acid with a hydrophobic side chain, and an amino acid with a hydrophilic side chain is preferably exchanged only with another amino acid with a hydrophilic side chain.

An amino acid sequence exhibiting homology above 40%, preferably more than 60%, and most preferably more than 70% (or any percentage greater than 70% but less than 100%) can be expected to be representative of a polypeptide exhibiting similar properties to a natural AFP (Qin et al., *Tenebrio molitor* antifreeze protein gene identification and regulation, *Gene* (2006) 367:142-149). In addition, the polypeptide encoded by the amino acid sequence should exhibit at least 40% (or any percentage greater than 40%) of the AFP activity of native AFP.

Activity of recombinant AFPs, engineered AFPs, antifreeze polypeptides and antifreeze peptides, active fragments of AFPs, antifreeze polypeptides and antifreeze peptides, mimetics of AFPs, antifreeze polypeptides and antifreeze peptides, their active mimetic fragments, AFP analogs and homologs, and combinations thereof can be determined by carrying out comparisons with ice affinity, thermal hysteresis (TH) measurements, or recrystallization assays using a series of dilutions of the polypeptide (to be determined) and equal amounts and dilutions of AFPs as obtained from natural sources. The manner in which the characteristics and/or properties in ice binding, TH, and ice recrystallization can be carried out and evaluated is known in the art.

In general, the non-antifreeze protein may comprise any protein with a therapeutic, medical or nutritional application. Non-antifreeze proteins used in the pharmaceutical industry may include, for example, enzymes such as alpha-1 antitrypsin, chymopapain, desmoteplase, ocriplasmin, or any other protein having biological catalytic activity. The non-antifreeze protein may include hormonal proteins such as insulin or a growth hormone (e.g., human growth hormone, bovine growth hormone, etc.), or any other protein having a cellular signaling or molecular transport activity. The non-antifreeze protein may include antibodies such as adalimumab, infliximab, and rituximab, or any other antibody used in antibody or monoclonal antibody therapy. The non-antifreeze protein may include proteins found in vaccinations or other autoimmune therapies such as hepatitis B, HPV and influenza vaccinations, or any other vaccination protein derived from viruses or bacteria.

The non-antifreeze protein may comprise proteins used in nutritional and/or food applications. For example, the non-antifreeze proteins may include proteins found in solid compositions such as whey or soy powder, tofu, beans, nuts, lentils, seeds, meats, fish, cheese, eggs, seafood, wheat germ and quinoa, and proteins found in liquid compositions such as milk, fermented yogurt beverages and protein shakes. In general, any animal, plant or fungal product commonly regarded as edible or potable may be a source of non-antifreeze protein.

The present composition may further include a solid or liquid excipient. An excipient may be a substance included with the active ingredient of a medication (e.g., in a pharmaceutical composition) for the purposes of long-term stabilization, to bulk up solid formulations that contain one or more active ingredients, or to confer a therapeutic enhancement on the active ingredient. Such enhancements may include facilitating drug absorption, reducing viscosity, and enhancing solubility.

Liquid excipients include deionized and/or distilled water, saline solutions (e.g., an isotonic solution of NaCl in deionized and/or distilled water) and/or saccharide solutions (e.g., aqueous solutions containing 1-20% by weight of glucose, fructose, mannitol, or other saccharide). Solid excipients include diluents (bulking agents), disintegrants, binders, lubricants, and glidants. Examples of solid excipients include sucrose, lactose, cellulose, hydroxypropyl methylcellulose (HPMC), starches, gelatin, xylitol, sorbitol, maltitol, shellac, zein, sodium starch glycolate, croscarmellose sodium, polyvinylpyrrolidone (PVP), polyethylene glycol (PEG), xanthan gum, magnesium stearate, and colloidal $SiO_2$. In general, the non-antifreeze protein may be combined with any solid or liquid excipient used in the pharmaceutical industry for the delivery of protein-based medicines.

The AFP may be combined with the non-antifreeze protein at a mass ratio from about 10:1 to 1:100 to form a mixture, although the invention is not limited thereto. For example, the mass ratio may be greater than 1:100 (e.g., 1:1000), as long as there is some protection against heat stress provided to the non-antifreeze protein. Alternatively, the AFP may be present at a ratio of the mass of the AFP to the volume of the composition in a range of 1:20 to 1:5,000,000. The components of the mixture may be mixed in a mixing apparatus such as a mill (e.g., when mixing solid components) or a vessel equipped with a mechanical or magnetic stirrer (e.g., when mixing one or more liquid components). The mixture may be stored in a container comprising glass, paper, plastic and/or metal. The container is generally sealed (e.g., with a cap, stopper, plug, septum, etc.). The mixture may be stored at temperatures ranging from freezing or below to ambient temperatures (e.g., 15-25° C.), although excursions to higher temperatures (e.g., around 30° C., 35° C., 40° C. or even 50° C.) are tolerable. Although a purpose of the invention is to protect the non-antifreeze protein against such temperature excursions, such excursions should be minimized (e.g., in number and/or length). The mixture may be stored for any length of time (e.g. from at least one minute, one hour, or one day, up to an indefinite amount of time).

EXPERIMENTAL SECTION

Materials

Lactate dehydrogenase (LDH, extracted from rabbit muscle) and alcohol dehydrogenase (ADH, extracted from *Saccharomyces cerevisiae*) were purchased from Sigma-Aldrich (St. Louis, Mo., USA). Two types of LDH products were used: a suspension of ammonium sulfate and a lyophilized powder. ADH was obtained as a lyophilized powder. The enzymes were used without further purification. BSA was purchased from Sigma-Aldrich (Item number A7030). Unless mentioned otherwise, all chemicals and reagents were obtained from Sigma-Aldrich (St. Louis, Mo., USA). All solutions were prepared using Milli-Q water produced from a Synergy water system (Millipore Co.) with a minimum resistivity of 18 MΩ·cm.

AFP Preparation

In general, AFPs can be prepared as described in Wang et al., "Molecular Recognition of Methyl α-D-Mannopyranoside by Antifreeze (Glyco)Proteins," *Journal of the American Chemical Society*, 136:8973-8981 (2014). Type I and type III AFPs were purchased from A/F Protein (Waltham, Mass.), which were used as received and/or according to Wang et al., *Chem. Commun.* 48:11555-11557 (2012). AFGPs were a gift. AFPs from *Dendroides canadensis* (DAFPs) and the meal worm *Tenebrio molitor* AFP (TmAFP) were prepared using the procedures as previously mentioned (Wang et al., *Biochemistry*, vol. 48 [2009], pp. 9696-9703; Zamalloa, Master's Thesis, Dept. of Chemistry, California State University—Los Angeles [2012]). *E. coli* Origami B cells harboring pET32b-DAFP-1, -2, -4 and TmAFP4-9 were briefly grown in lysogeny broth (LB) media supplemented with kanamycin (15 µg/mL) and ampicillin (50 µg/mL). Isopropyl β-D-1-thiogalactopyranoside (IPTG) (0.5 mM) was added to the culture to induce a high-level expression of AFPs when OD600 (absorbance at 600 nm) reached 0.6. The cells were harvested by centrifugation at 4° C. The cells were disrupted mechanically by two passes through a French press (Thermo Fisher) or by using lysozyme. The crude protein was purified using nickel-nitrilotriacetic-acid (Ni-NTA) agarose. The terminal tag (containing the hexahistidine) was cleaved using enterokinase (New England Biolabs) and removed using Ni-NTA agarose (Qiagen). The cleaved protein was then purified by AKTA Purifier 10 (GE Healthcare) using a Sephacryl S-100 gel filtration column (GE Healthcare). The protein concentration was determined by UV-Vis spectroscopy using the absorption at 280 nm.

Sample Preparation and Enzyme Assays

Heat treatments were performed in a water bath (Precision™) or a PCR thermal cycler. LDH (e.g., 1-200 µg/ml) samples in the absence and presence of various AFPs (e.g., 1-200 µg/ml) were heated at one of a plurality of different temperatures (e.g., 40, 46, 50, or 60° C.) over a range of durations (0-60 min) at each temperature. The samples were cooled down to room temperature before activity assays were conducted.

LDH is found in nearly all living cells including animals, plants, and prokaryotes. LDH catalyzes the conversion of lactate ($C_3H_5O_3$) to pyruvic acid ($C_3H_4O_3$) and back as it converts $NAD^+$ to NADH and back. LDH assays were generally performed following a published protocol (Bergmeyer et al., *Methods of Enzymatic Analysis*, Verlag Chemie [1974], pp. 574-579). A sample reaction cocktail for LDH assay consisted of 9.9 ml 0.14 M CAPS buffer (pH 10), 2.3 ml 6 mM NAD+, and 2.3 ml 150 mM lactate. The formation of NADH was detected at 340 nm using UV-Vis spectroscopy.

ADH is found in high concentrations within the human liver and kidney, where its primary role is to detoxify ethanol. ADH can convert ethanol into acetaldehyde, which is then quickly converted into acetate and other molecules that are easily utilized by the cell. ADH assays were generally performed following a published protocol (Kagi et al., *J. Biol. Chem.*, vol. 235 [1960], pp. 3188-3192). ADH (e.g., 0.5-100 µg/ml) samples in the absence and presence of various AFPs (e.g., 0.5-100 µg/ml) were stored or heated at various temperatures (e.g., 22, 30, 40, 46, 50, or 60° C.) over a range of durations at each temperature (0-60 min). The samples were cooled down to room temperature before activity assays were conducted.

Notably, bovine serum albumin (BSA) is used as a stabilizer for enzymes in these published protocols. Here, no BSA was added unless specified otherwise. Enzyme activities were assayed using an Eppendorf spectrophotometer with a thermostated cell compartment at 25° C. The freeze-thaw experiments are described in the examples below.

Example 1. Protection for Proteins Under Temperature Stress by AFPs

Proteins, including enzymes, are utilized in a variety of applications (e.g., diagnostic, therapeutic, foods, and animal feeds/nutrition). For example, the potential commercial applications of enzymes for maximizing animal performance through the improvement of nutrient digestion is significant. In another example, the enzyme glucose oxidase is used in diagnostic applications, such as (or including) glucose assays. The hormone insulin is an example of a protein utilized in therapeutic applications. Unfortunately, the main obstacle for the full development of these markets is the observation that many proteins are intrinsically unstable (see, e.g., WO 2003/040398 A2 and U.S. Pat. No. 8,399,230 B2). AFPs show a highly effective thermoprotective effect on the activity of enzymes in model systems, namely lactate dehydrogenase (LDH) and alcohol dehydrogenase (ADH), and can be used to protect other proteins in general against thermal deactivation.

Figure 2:
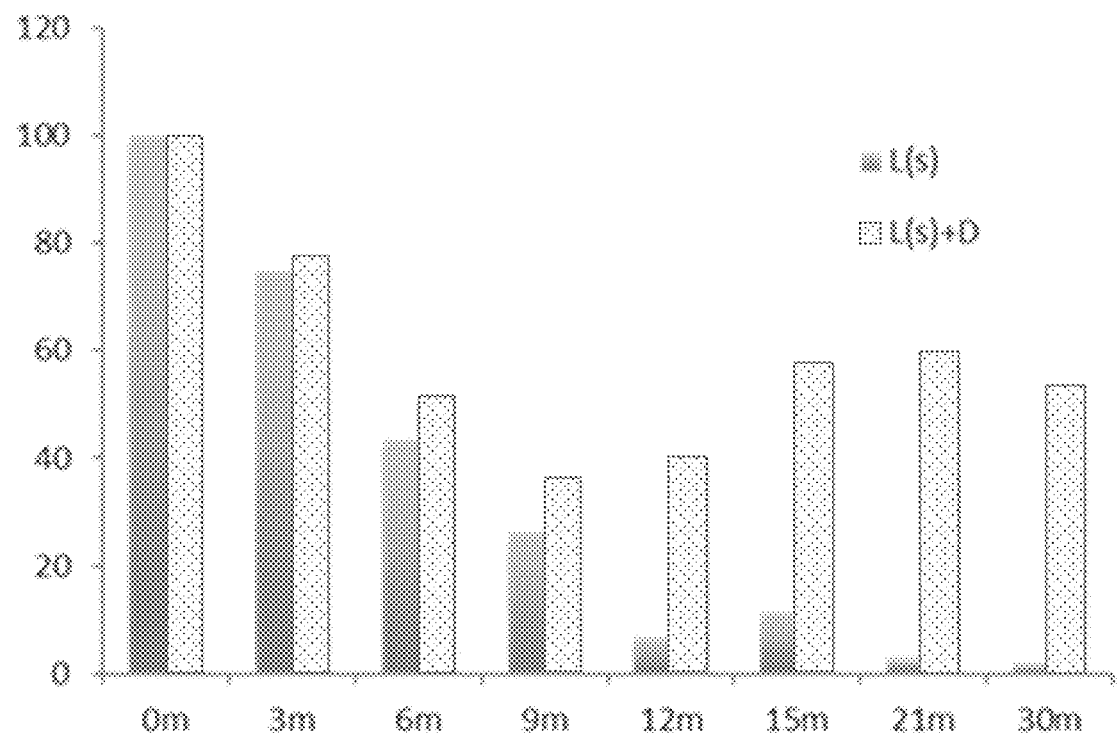
FIG. 2 is a bar graph showing an LDH activity assay after heat treatment for 0-30 min at 40° C. in the absence or presence of DAFP-1. The graph is plotted as % LDH activity vs. time, where L(s) represents LDH alone and L(s)+D represents LDH in the presence of DAFP-1.

FIG. 2 shows the results of LDH activity assays after heat treatment for 0-30 min at 40° C. "L(s)" represents LDH alone. "L(s)+D" represents LDH in the presence of DAFP-1. The data bars for "L(s)" are shown in lighter grey on the left, while the data bars for "L(s)+D" are shown in darker grey on the right. The LDH in this assay was prepared from a lyophilized powder. The concentration of LDH is 40 µg/mL, and concentration of DAFP-1 is 0.003% w/v.

Figure 3:
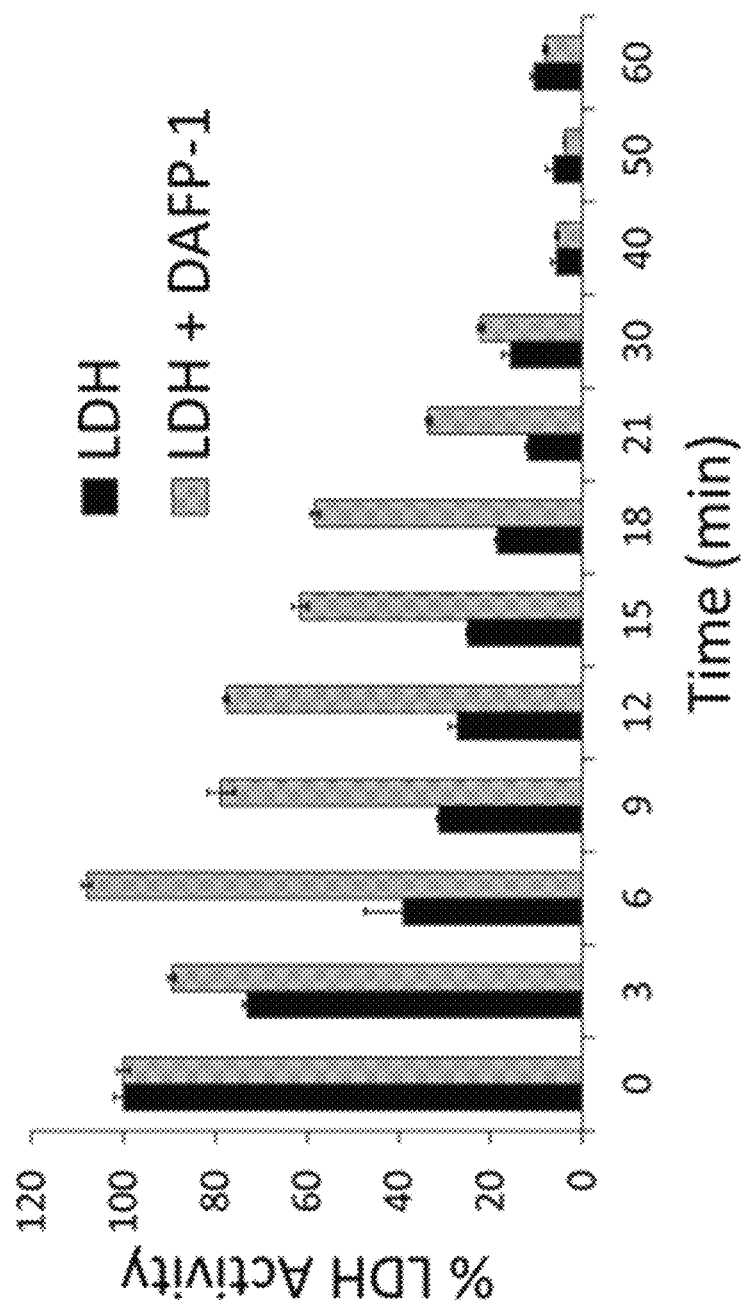
FIG. 3 is a bar graph showing an LDH activity assay after heat treatment for 0-60 min at 50° C. in the presence of DAFP-1 (DAFP-1 extends LDH activity for about 6 times longer than in the absence of DAFP-1).

FIG. 3 shows the results of LDH activity assays after heat treatment for 0-60 min at 50° C. "LDH" represents LDH alone. "LDH+DAFP-1" represents LDH in the presence of DAFP-1. The LDH in this assay was prepared from a suspension in ammonium sulfate. The concentration of LDH is 40 µg/mL, and concentration of DAFP-1 is 0.003% w/v.

Figure 4:
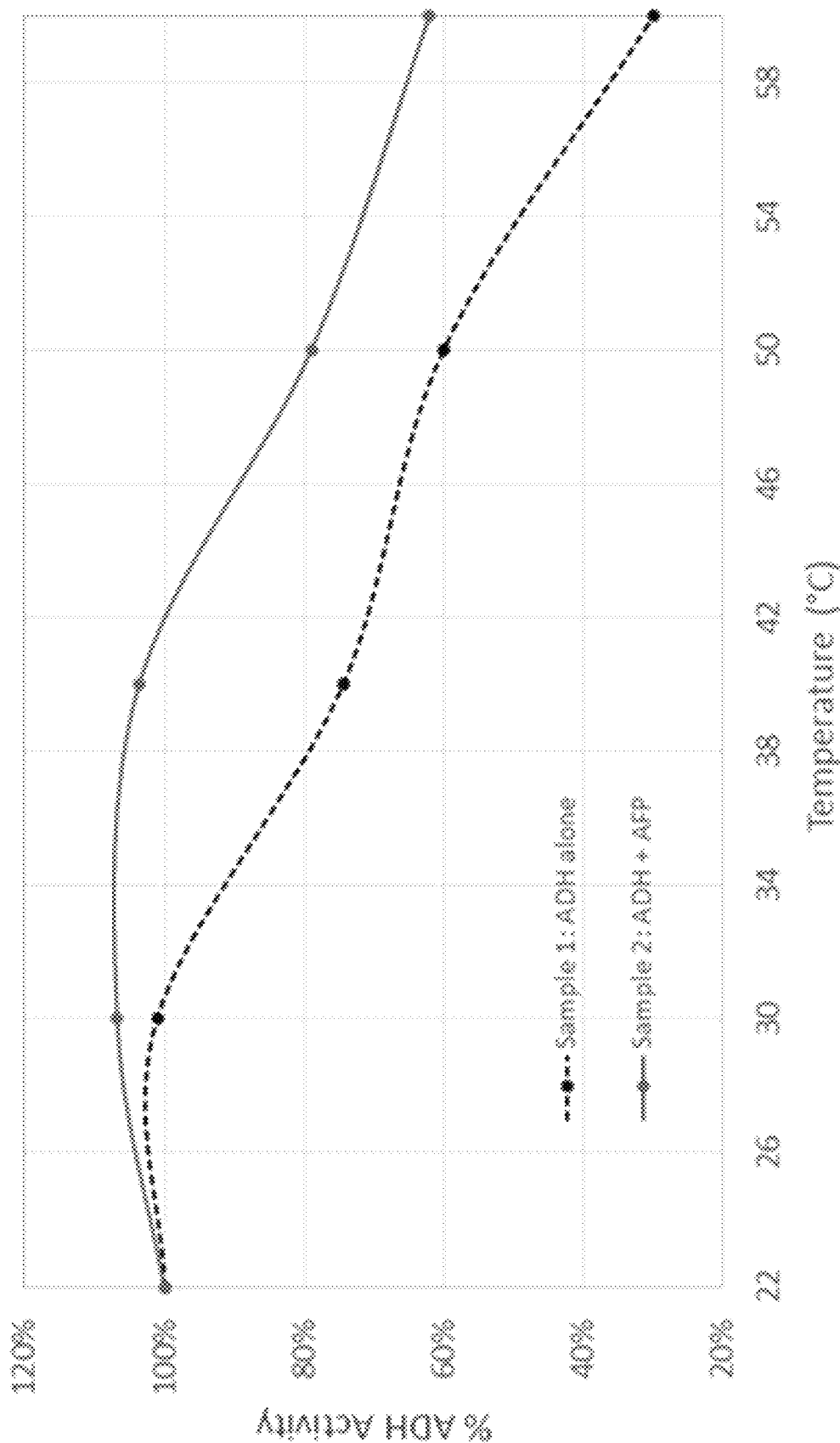
FIG. 4 is a graph showing sample ADH activity assays after heat treatment for 10 min at various temperatures (from room temperature to 60° C.) in the absence and presence of DAFP-1.

FIG. 4 shows the results of ADH activity assays after heat treatment for 10 min at various temperatures (from room temperature to 60° C.) in the absence and presence of an AFP (DAFP-1). The dashed (lower) line represents the enzyme activity of alcohol dehydrogenase (ADH) alone. The light, smoothed (higher) line represents the enzyme activity of alcohol dehydrogenase (ADH) in the presence of DAFP-1. In the presence of AFP, ADH retains its activity at significantly high levels, even at 50° C. or 60° C. (e.g., above 60% of its activity). The concentration of ADH is 0.5 μg/mL, and concentration of DAFP-1 is 0.000025% w/v.

Example 2. Protection for Proteins Under Freeze/Thaw Stress by AFPs

During the freezing process of a solution containing water, ice will usually form. The presence of ice will destabilize various biologics, such as therapeutic proteins, enzymes, cells, tissues, and organs (Ratanji et al., "Immunogenicity of therapeutic proteins: Influence of aggregation," J Immunotoxicol., 2014 April; 11(2): 99-109.).

As previously mentioned, AF(G)Ps are characterized by their ability to specifically bind to ice. AF(G)Ps may protect biologics under freeze/thaw stress by avoiding the direct exposure of delicate biologics to ice. We have successfully demonstrated that AFPs can protect biologics under freeze/thaw stress.

AFPs show a cryoprotective effect on the activity of enzymes in model systems (e.g., lactate dehydrogenase [LDH]), and can be used to protect enzymes in general against freezing and thawing deactivation. The protective effects of AFPs are greater than those of commonly used protectants or stabilizers (e.g., BSA, sucrose). The data shown below are averages of at least three experiments, with a standard deviation less than 0.02%.

Figure 5:
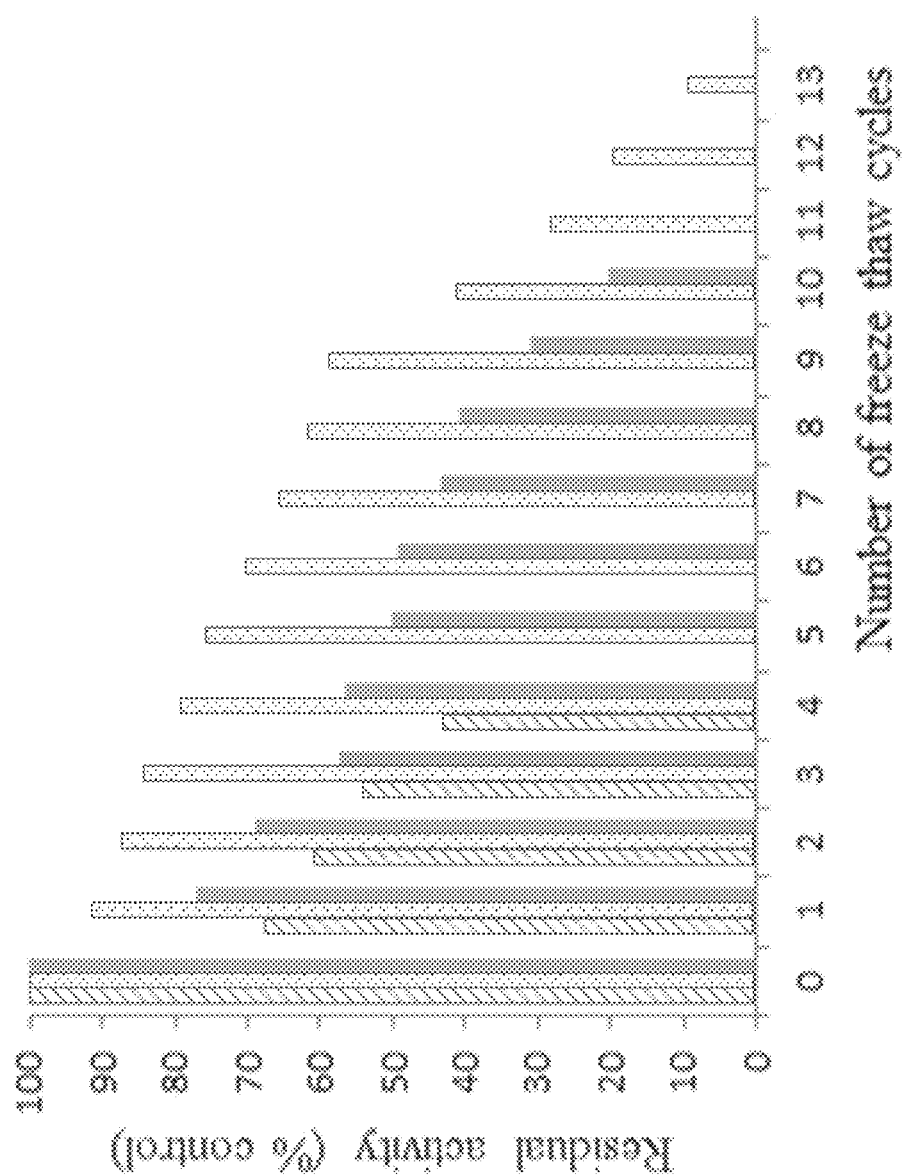
FIG. 5 is a bar graph showing an LDH activity assay after freeze-thaw treatment cycles in the presence of DAFP-1 or a macromolecule protectant, BSA.

FIG. 5 shows the results of LDH activity assays after successive cycles of freeze-thaw treatment using DAFP-1 or BSA as a protective agent against freeze-thaw stress. BSA is a commonly used protectant molecule, and is widely commercially available. The enzyme samples were frozen at −20° C. for 16 hours in each freeze-thaw cycle. The left-hand bar in each cycle represents the data for LDH alone (50 μg/ml), the center bar represents the data for LDH (50 μg/ml) and BSA (0.5% w/v), and the right-hand bar represents the data for LDH (50 μg/ml) and DAFP (0.0025% w/v). The left-hand bars, representing the data for samples containing LDH alone, show the lowest activity during cycles 1-4 and are shown only in cycles 0-4. The samples of LDH alone have the least resistance to freezing-thawing stress and completely lose activity after 4 cycles of freezing-thawing. The center bars, representing the data for LDH (50 μg/ml) in the presence of BSA (0.5% w/v), show the second lowest activity and resistance to freezing-thawing stress. The activity of the samples containing LDH and BSA disappears after 10 cycles of freezing-thawing. The right-hand bars, representing the data for LDH (50 μg/ml) in the presence DAFP (0.0025% w/v), show the highest activity during all of the freezing-thawing cycles (i.e., 1-13) and thus the highest resistance to freezing-thawing stress. The testing was stopped after 13 cycles. Moreover, the residual activity of LDH in the presence of DAFP-1 is significantly higher than in the presence of BSA (at least 12% or higher) during the freeze-thaw treatments.

Figure 6:
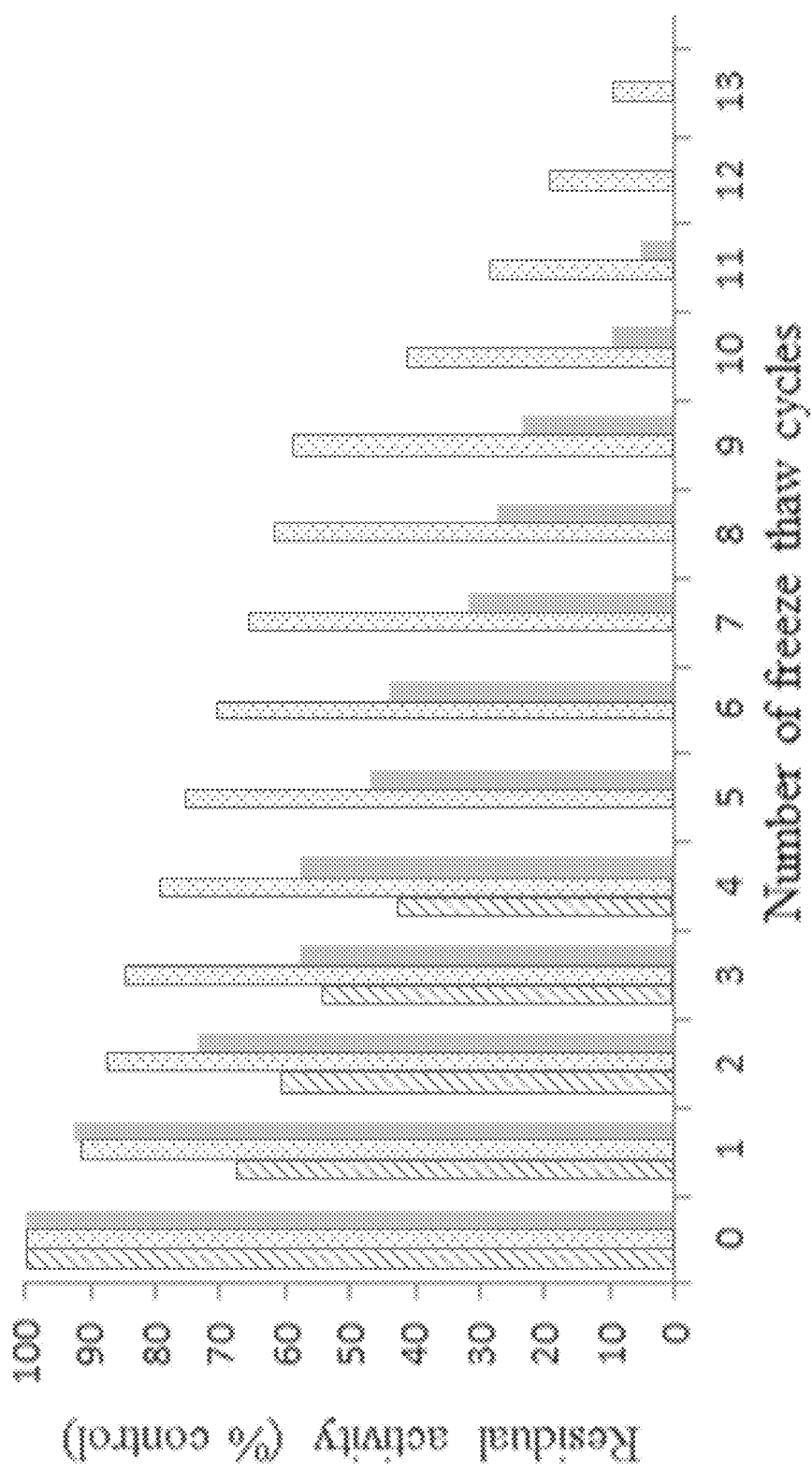
FIG. 6 is a bar graph showing an LDH activity assay after freeze-thaw treatment cycles in the presence of DAFP-1 or a small molecule protectant, sucrose.

FIG. 6 shows the results of LDH activity assays after successive cycles of freeze-thaw treatment using DAFP-1 or sucrose as a protective agent against freeze-thaw stress. Sucrose is a commonly used protectant molecule, and is widely commercially available. The enzyme samples were frozen at −20° C. for 16 hours in each freeze-thaw cycle. Data was not collected beyond cycle 13. The left-hand bar in each cycle represents LDH alone (50 μg/ml), the center bar represents LDH (50 μg/ml) and DAFP (0.0025% w/v), and the right-hand bar represents LDH (50 μg/ml) and sucrose (10% w/v). The left-hand bars, representing the data for LDH alone samples, show the lowest activity and freezing-thawing resistance during cycles 1-4. The left-hand bars are shown only in cycles 0-4 as the samples of LDH alone completely lose activity after 4 cycles of freezing-thawing. The center bars, representing the data for LDH (50 μg/ml) and DAFP (0.0025% w/v), show the highest activity and resistance to freezing-thawing stress during almost all of the freezing-thawing cycles (i.e., 1-13). The testing was stopped after 13 cycles. The right-hand bars, representing the data for LDH (50 μg/ml) in the presence of sucrose (10% w/v), show the second lowest activity and resistance to freezing-thawing stress. The activity of the samples containing LDH and sucrose completely disappears after 11 cycles of freezing-thawing. Moreover, the residual activity of LDH in the presence of DAFP-1 is significantly higher than in the presence of sucrose (e.g., at least 15% or higher) during the freeze-thaw treatments in general.

Example 3. Protection for Microbes Under Freeze/Thaw Stress by AFPs

This example shows that TmAFP protects microbes. Bacterial cells (e.g., DH5α, BL21) were used as model cell systems from freezing and thawing. For example, DH5α competent cells are often used for general cloning and subcloning, and BL21 strains are descended from the E. coli B strain and have been specifically constructed for high-level expression of recombinant proteins with two important attributes that make them ideal for protein expression (e.g., key genetic markers and inducibility of protein expression). The cell viability of these cells was assayed by counting the number of isolated bacterial colonies per area of LB agar plate.

The bacteria cells were grown in LB media with appropriate amounts of antibiotics. For example, ampicillin (100 μg/ml) and kanamycin (30 μg/ml) were added to LB media inoculated with E. coli (DH 5α pET 28a), which were grown overnight at 37° C. 800 μL of the cell culture were transferred into each sterilized microcentrifuge tube. Equal volumes of water, a commonly used cryoprotectant, and AFP were then added into the microcentrifuge tubes, respectively. The samples were then treated by freezing at −20° C. for 20 min and then thawing at 20° C. for 20 min for four times per day and every day for a week.

Figure 7:
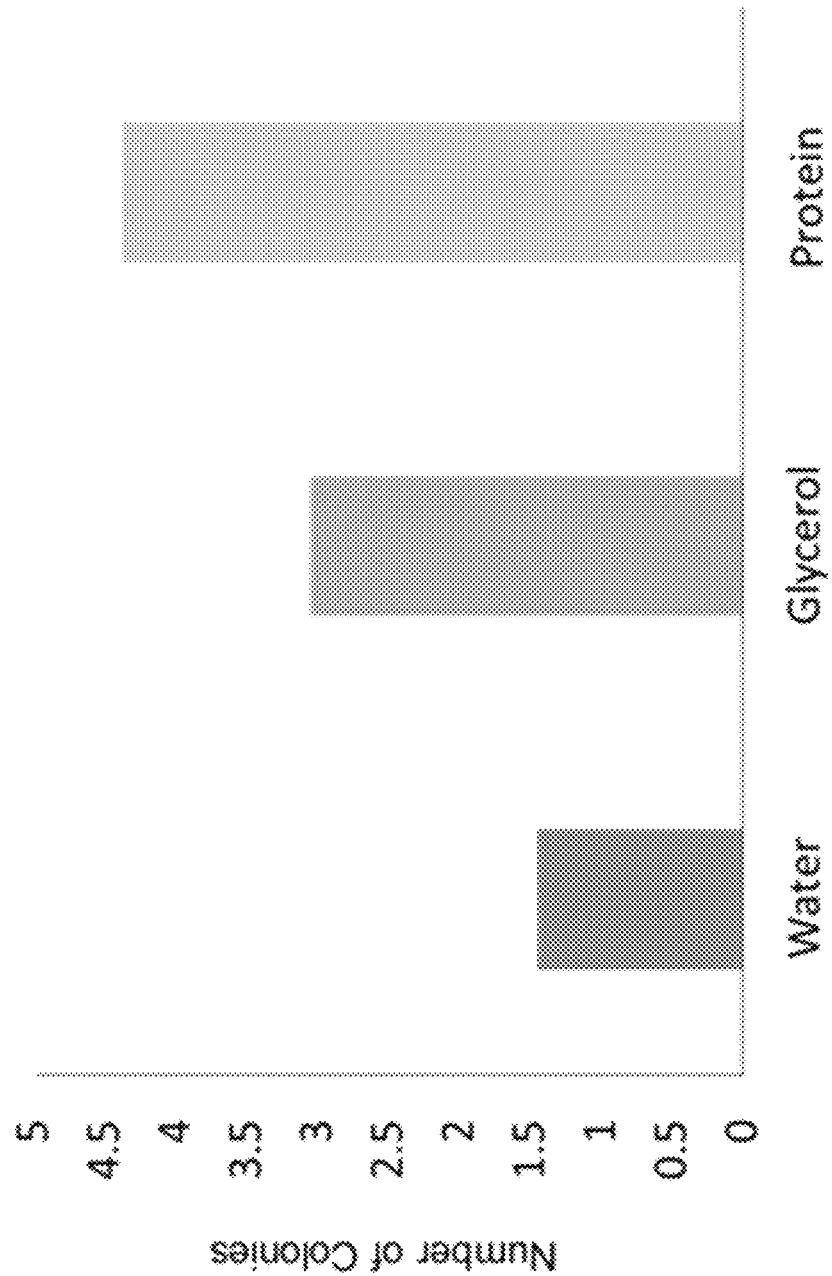
FIG. 7 is a bar graph showing the viability of cell culture samples of *E. coli* cells after twenty-eight short freeze-thaw (or heated-shocked) cycles in a week.

FIG. 7 shows the E. coli cell viabilities of the cell culture samples treated after twenty-eight freezing-thawing cycles. The numbers of single colonies shown in FIG. 7 were observed after streaking an LB agar plate with solutions of the above samples diluted to 25,000× and counting the bacterial colonies per $cm^2$. "Water" represents the sample containing the cell culture and water. "Glycerol" represents the sample containing the cell culture and glycerol (20% v/v). "Protein" represents the sample containing the cell culture and TmAFP (0.001% w/v). The averages of two measurements are shown in FIG. 7. The presence of an AFP significantly improves the viability of the cells (e.g., by about 300% under the testing conditions).

Example 4. Protection Against Protein Aggregation by AFPs

Proteins have an increased tendency to unfold under stress situations (e.g., exposure to heat, ice, temperature fluctuations during transportation or storage, oxidative stress, radiation, or shear forces). As proteins misfold and self-associate, they may form either amorphous aggregates or highly structured, protease-resistant fibrils known as amyloids or amyloid proteins. Amorphous protein aggregates are unable to perform their biological role and may physically obstruct physiological functions. While the process of amyloid formation may produce intermediates that are directly toxic to cells and that causes or may cause disease (e.g., Alzheimer's disease, the synucleinopathies, the systemic amyloidoses, and the pathogenesis of type 2 diabetes mellitus; see Finn et al., *J. Biol. Chem.* [2012] 287:25, 21530-21540).

Protein aggregation has been a major challenge in the development of biologic formulations and products, because it can have an impact on product quality in terms of efficacy and immunogenicity. Therefore, effective additives, excipients, or protective agents may be required in various formulations and products with biologics (e.g., enzymes, vaccines, cells, tissues, pharmaceutical formulations, functional foods, nutrients, food formulations). Various protective agents have been used in the art, and the degree of success of these agents are varied. For example, glycerol, albumins, and disaccharides are common protectants in various formulations and products.

We have demonstrated that AFPs protect against protein aggregation. Aggregation assays were performed for alcohol dehydrogenase (ADH) at a concentration of 350 μg/ml. A serum albumin protein, bovine serum albumin (BSA) at a concentration of 0.25% w/v and a disaccharide, trehalose, at a concentration of 0.15% w/v are used here for comparison. Both BSA and trehalose are commonly used, generally effective protective agents.

The samples were heated at 50° C. The time was recorded from the time that the samples were heated. Protein aggregate turbidity was monitored by absorbance at 360 nm as a function of time.

Figure 8:
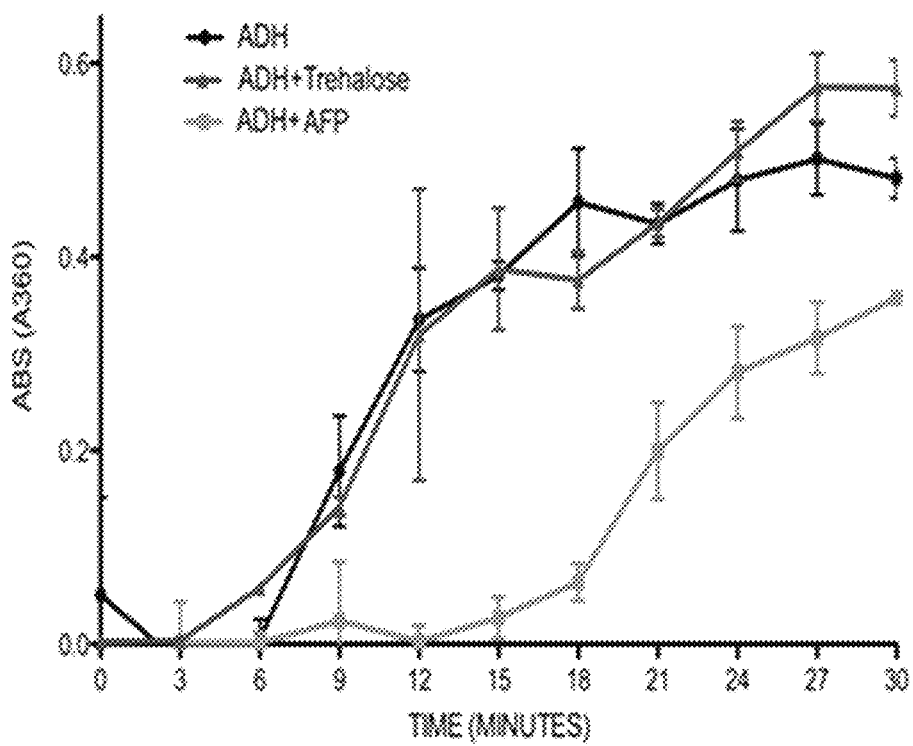
FIGS. 8 and 9 are graphs showing the anti-aggregation of other proteins (alcohol dehydrogenase [ADH], 350 µg/ml) by an AFP (DAFP-1) at 50° C.
Figure 9:
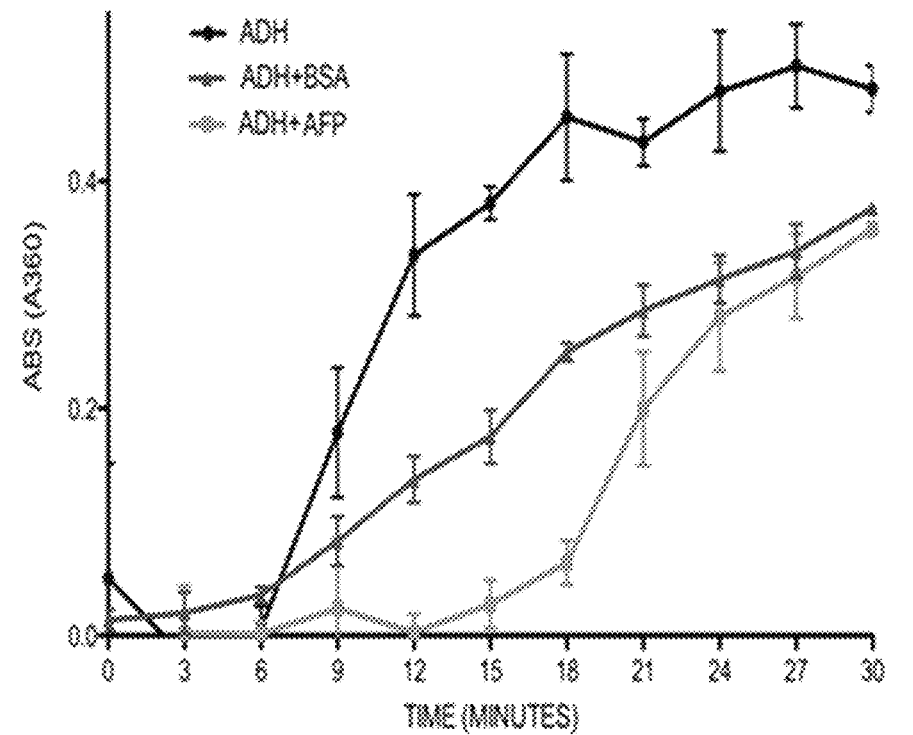

FIGS. 8 and 9 are graphs showing the aggregation of alcohol dehydrogenase (ADH) at 350 μg/ml and the anti-aggregation activity of DAFP-1 and either trehalose (FIG. 8) or bovine serum albumin (BSA; FIG. 9) during heat treatment of ADH at 50° C. The black lines with circular data points are for ADH alone. The blue lines with triangular data points are for ADH+trehalose (1.5 mg/ml; FIG. 8) or ADH+BSA (0.25% w/v; FIG. 9). The light green lines with square data points are for ADH+DAFP-1 (0.006% w/v).

As shown in FIGS. 8 and 9, ADH aggregates during the process. At 0.15% w/v, trehalose shows little protective effect against the aggregation (FIG. 8). At 0.25% w/v, BSA shows some protective effect against the aggregation (FIG. 9). At a much lower concentration (0.006% w/v), DAFP-1 shows much more significant anti-aggregation effect than the more-common protective agents (FIGS. 8 and 9).

Figure 10:
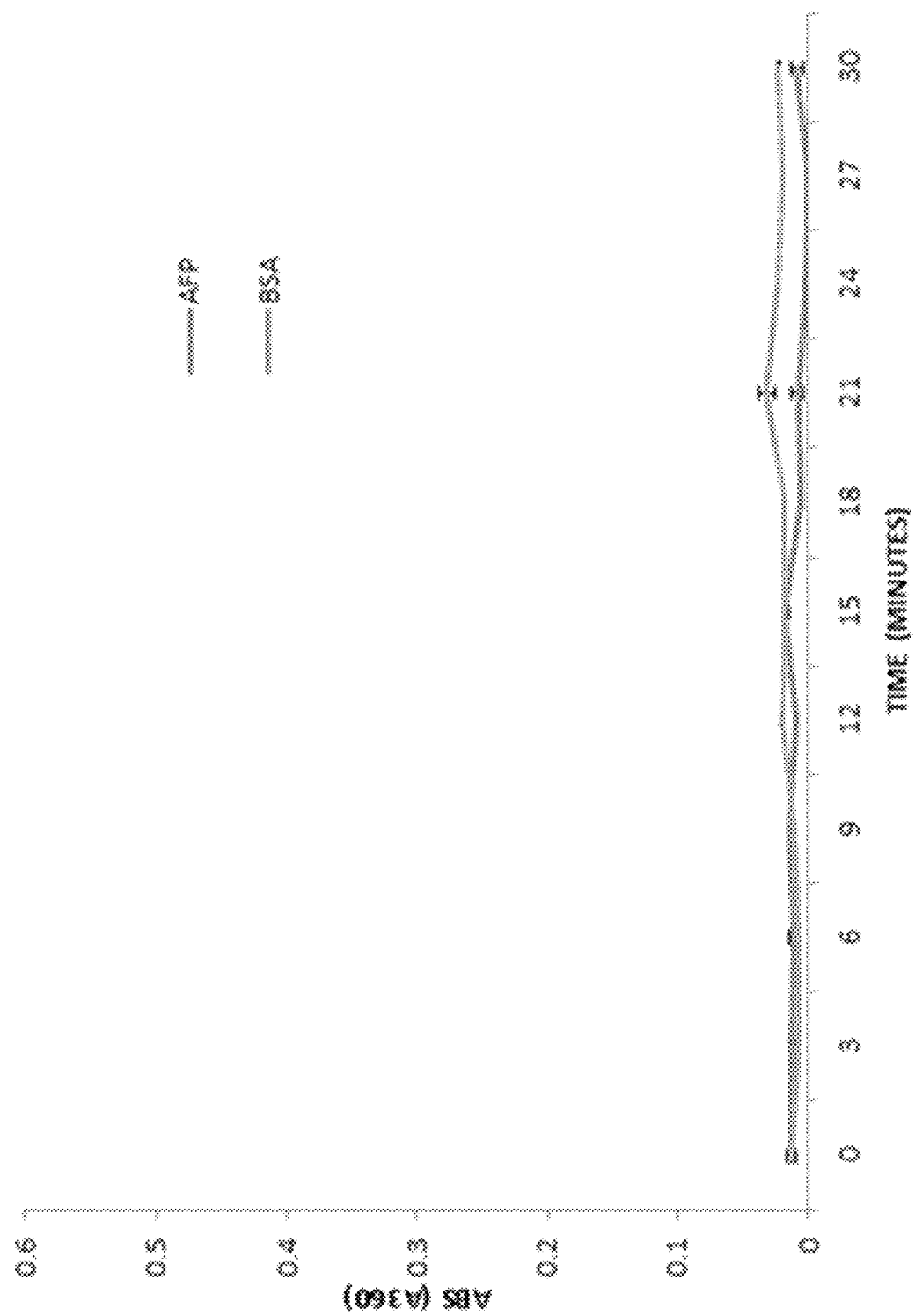
FIG. 10 is a graph showing the results of aggregation assays of an AFP (0.006% w/v) and BSA (0.25% w/v) at 60° C.

Both AFP and BSA are very stable proteins. No protein aggregate turbidity was observed during the heat process of either protein, even at 60° C. (FIG. 10).

Other available AFPs (e.g., DAFP isoforms, TmAFPs, type III AFPs, AFGPs) show a similar protective effect against other protein aggregations. The degree of effectiveness of AFPs other than DAFP-1 vary, but other AFPs exhibit effective anti-aggregation activity at concentrations of, for example, from 0.001% to 1% w/v.

Example 5. Protection for Mammalian Cells During Preservation

Cells obtained by either cultivation or extraction from mammalian tissues (e.g., human or animal) are often used in the fields of regenerative medicine and livestock farming. For some cases, it is desirable to preserve these cells without freezing (e.g., for short-term transplantations). Generally, these cells are handled as assemblies of several cells to millions of cells, and the percentage of viable cells in the total number (i.e., the viability rate) can be improved by soaking them in a preservation solution comprising inorganic salts, glycerol, one or more sugars, etc. Commonly-used preservation solutions include lactated Ringer's, Celsior, Euro-Collins (EC), the University of Wisconsin (UW), and histidine-tryptophan-ketoglutarate (HTK) solutions. These solutions were originally developed to preserve specific organs, but have now been used for preserving various types of cells, tissues, and organs, despite the fact that their optimal performance depends on the type of cells, the tissue, or the organ. For example, EC and UW solutions may preserve human hepatocytes under hypothermic conditions (e.g., 4° C.) for 1-3 days (i.e., 24 h to 72 h).

Insulinoma cell lines display many important characteristics of the pancreatic beta cell, including a high insulin content and responsiveness to glucose (associated with expression of GLUT-2 and glucokinase) within physiological ranges. The rat insulinoma cell line INS-1 is the most commonly used clonal cell model in pancreatic β-cell research.

In the present study, INS-1 cells were cultured and placed into 96-well microplates for 24 hours of incubation at 37° C. and 5% $CO_2$. After a day of adhering to the microplate, the media was aspirated, and then UW solution was added to the cells. One UW solution included TmAFP; one did not. The cells were then stored at 4° C. for up to 7 days. The viability of the cells was evaluated by trypan blue staining using a Nexcelom Cellometer. The viability of the cells was greatly prolonged in the presence of only about 0.005% (w/v) TmAFP (Table 1).

TABLE 1

Sample results for cell viability rates of a mammalian cell line under hypothermic exposure (4° C.) in the presence of TmAFP[a]:

|  | INS-1 cells in UW solution | INS-1 cells in UW solution + TmAFP (50 μg/mL)[b] |
|---|---|---|
| Day 0 (0 h) | 100% | 100% |
| Day 5 (120 h) | 81% | 95% |
| Day 6 (144 h) | 75% | 96% |
| Day 7 (168 h) | 63% | 79% |

[a]The viability of cells is normalized to untreated cells on Day 0 (0 h).
[b]Although the data shown in Table 1 is for TmAFP4-9, DAFPs show a similar effect at similar concentrations. The degree of effectiveness of other AFPs (e.g., type I AFPs, type III AFPs, AFGPs) is generally lower. That is, higher concentrations (e.g., from 0.5% to 5% w/v) are needed for protection of the cell line, and such effectiveness is generally for a shorter period of time (e.g., until day 5 or day 6).

CONCLUSION/SUMMARY

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

The invention claimed is:

1. A composition, comprising:
   an antifreeze protein (AFP) selected from the group consisting of natural or engineered SEQ ID NO: 1 (DAFP-1), SEQ ID NO: 2 (DAFP-2), SEQ ID NO: 3 (DAFP-4) and SEQ ID NO: 4 (DAFP 6); and
   a non-antifreeze protein selected from the group consisting of enzymes, hormones, antibodies, growth factors, therapeutic proteins, nutrient proteins and food proteins in need of protection against heat stress;
   wherein the antifreeze protein and the non-antifreeze protein are present in a mass ratio of from 1:1 to about 1:1000.

2. The composition of claim 1, wherein the non-antifreeze protein comprises an enzyme, hormone, antibody, growth factor, or therapeutic protein.

3. The composition of claim 1, wherein the AFP is natural or engineered SEQ ID NO:1 (DAFP-1).

4. The composition of claim 1, wherein the AFP is natural SEQ ID NO: 1 (DAFP-1), natural SEQ ID NO: 2 (DAFP-2), natural SEQ ID NO: 3 (DAFP-4), or natural SEQ ID NO: 4 (DAFP-6).

5. The composition of claim 1, wherein the AFP is engineered SEQ ID NO: 1 (DAFP-1), engineered SEQ ID NO: 2 (DAFP-2), engineered SEQ ID NO: 3 (DAFP-4), or engineered-SEQ ID NO: 4 (DAFP-6).

6. The composition of claim 1, wherein the non-antifreeze protein is a nutrient or food protein selected from the group consisting of whey proteins, tofu proteins, meat proteins, milk proteins, and fermented yogurt proteins.

7. The composition of claim 1, comprising a food selected from the group consisting of tofu, beans, nuts, lentils, seeds, meats, fish, cheese, eggs, seafood, wheat germ and quinoa, milk, whey powder, and fermented yogurt beverages, wherein the non-antifreeze protein is in the food.

8. The composition of claim 2, wherein the non-antifreeze protein comprises alpha-1 antitrypsin, chymopapain, desmoteplase, ocriplasmin, insulin, a growth hormone, an IgG antibody, an IgE antibody, an IgA antibody, an IgM antibody or an IgD antibody.

9. A formulation, comprising the composition of claim 1 in a pharmaceutically acceptable, nutritionally acceptable, or biologically-compatible excipient, carrier, or adjuvant or combination thereof.

10. The formulation of claim 9, wherein the excipient comprises deionized water, distilled water, starch, a saccharide, a sugar alcohol, gelatin, polyvinylpyrrolidone (PVP), cellulose, a cross-linked polyvinylpyrrolidone, a cross-linked carboxymethyl cellulose, hydroxypropyl methylcellulose, polyethylene glycol, magnesium stearate or colloidal $SiO_2$, and a ratio of the AFP to a volume of the formulation is 1:20 to 1:5,000,000 weight to volume.

11. A composition, comprising:
    an antifreeze protein (AFP) selected from the group consisting of natural or engineered SEQ ID NO: 1 (DAFP-1), SEQ ID NO: 2 (DAFP-2), SEQ ID NO: 3 (DAFP-4) and SEQ ID NO: 4 (DAFP-6); and
    a microbe or a cell selected from the group consisting of viruses, bacteria cells, plant cells, blood cells, stem cells, egg cells, fungal cells, mold cells, and animal cells;
    wherein the ratio of the mass of the AFP to the volume of the composition is in a range of 1:20 to 1:5,000,000.

12. The composition of claim 11, wherein the microbe or the cell comprises live or dead bacteria or viruses.

13. The composition of claim 11, wherein the AFP is engineered SEQ ID NO: 1 (DAFP-1), SEQ ID NO: 2 (DAFP-2), SEQ ID NO: 3 (DAFP-4) or SEQ ID NO: 4 (DAFP-6).

14. The composition of claim 11, wherein the AFP is engineered SEQ ID NO: 1 (DAFP-1).

15. The composition of claim 11, wherein the ratio of the mass of the AFP to the volume of the composition is from 1:1000 to 1:200,000.

16. The composition of claim 11, wherein the AFP is natural SEQ ID NO: 1 (DAFP-1), SEQ ID NO: 2 (DAFP-2), SEQ ID NO: 3 (DAFP-4) or SEQ ID NO: 4 (DAFP-6).

17. The composition of claim 16, wherein the AFP is natural SEQ ID NO: 1 (DAFP-1).

18. The composition of claim 11, wherein the microbe or cell is a virus or bacteria cells.

* * * * *